US012807922B2

(12) United States Patent
Haupt

(10) Patent No.: US 12,807,922 B2
(45) Date of Patent: Nov. 24, 2026

(54) EXPANSION OF STEM CELLS IN SUSPENSION IN A BIOREACTOR

(71) Applicant: REPAIRON GMBH, Gottingen (DE)

(72) Inventor: Luis Haupt, Gottingen (DE)

(73) Assignee: REPAIRON GMBH, Gottingen (DE)

( * ) Notice: Subject to any disclaimer, the term of this patent is extended or adjusted under 35 U.S.C. 154(b) by 839 days.

(21) Appl. No.: 17/757,141

(22) PCT Filed: Dec. 11, 2020

(86) PCT No.: PCT/EP2020/085667

§ 371 (c)(1),
(2) Date: Jun. 9, 2022

(87) PCT Pub. No.: WO2021/116362

PCT Pub. Date: Jun. 17, 2021

(65) Prior Publication Data

US 2023/0059873 A1 Feb. 23, 2023

(30) Foreign Application Priority Data

Dec. 11, 2019 (EP) .................................... 19215091

(51) Int. Cl.
*C12N 5/0735* (2010.01)
*C12N 5/074* (2010.01)

(52) U.S. Cl.
CPC ......... *C12N 5/0606* (2013.01); *C12N 5/0696* (2013.01); *C12N 2500/30* (2013.01); *C12N 2501/727* (2013.01)

(58) Field of Classification Search
None
See application file for complete search history.

(56) References Cited

U.S. PATENT DOCUMENTS

| | | | | |
|---|---|---|---|---|
| 2011/0263016 | A1 | 10/2011 | Rancourt et al. | |
| 2016/0340633 | A1 | 11/2016 | Davis et al. | |
| 2019/0031990 | A1 | 1/2019 | Timmins et al. | |
| 2019/0359946 | A1* | 11/2019 | Nie | C12N 5/0663 |

FOREIGN PATENT DOCUMENTS

| | | | | |
|---|---|---|---|---|
| EP | 3202896 | A1 * | 8/2017 | C12M 3/00 |
| WO | 2010/035136 | A2 | 4/2010 | |
| WO | 2012/158899 | A1 | 11/2012 | |
| WO | 2014/106141 | A1 | 7/2014 | |
| WO | 2015/134652 | A1 | 9/2015 | |
| WO | 2016/113369 | A1 | 7/2016 | |
| WO | WO-2017127921 | A1 * | 8/2017 | C12M 27/02 |
| WO | 2018/136500 | A1 | 7/2018 | |

OTHER PUBLICATIONS

Yang et al (Cell 169, 243-257, Apr. 6, 2017, Doi: 10.1016/j.cell.2017.02.005). (Year: 2017).*
Zhang et al (PLoS One 6(3): e18271. doi:10.1371/journal.pone.0018271, Mar. 28, 2011) (Year: 2011).*
Milteny (StemMACS iPS-Brew XF Xeno- and feeder-free culture of human ES and iPS cells, 2014) (Year: 2014).*
Lonza (Certificate Of Analysis, Product Code: TC-1133 Lot No. 50-001-21, P20, Edition: Feb. 25, 2016). (Year: 2016).*
International Search Report issued in PCT/EP2020/085667 on Mar. 12, 2021 (5 pages).
Chen et al., "Development of a scalable suspension culture for cardiac differentiation from human pluripotent stem cells", Stem Cell Res. Sep. 2015;15(2):365-75. doi: 10.1016/j.scr.2015.08.002. Epub Aug. 13, 2015.
Kropp et al., "Progress and challenges in large-scale expansion of human pluripotent stem cells", Process Biochemistry, 59:244-254, 2017.
Written Opinion issued in PCT/EP2020/085667 on Mar. 12, 2021 (6 pages).
Baghbaderani et al., cGMP-Manufactured Human Induced Pluripotent Stem Cells Are Available for Pre-clinical and Clinical Applications. Stem Cell Reports. Oct. 13, 2015;5(4):647-659.
Burridge et al., Chemically Defined Culture and Cardiomyocyte Differentiation of Human Pluripotent Stem Cells. Curr Protoc Hum Genet. Oct. 6, 2015;87:21.3.1-21.3.15.
Chou et al., Efficient human iPS cell derivation by a non-integrating plasmid from blood cells with unique epigenetic and gene expression signatures. Cell Res. Mar. 2011;21(3):518-529.
Didié et al, Parthenogenetic stem cells for tissue-engineered heart repair. J Clin Invest. Mar. 2013;123(3):1285-1298.
Espejel et al., Parthenogenetic embryonic stem cells are an effective cell source for therapeutic liver repopulation. Stem Cells. Jul. 2014;32(7):1983-1988.
Kang et al., Improving Cell Survival in Injected Embryos Allows Primed Pluripotent Stem Cells to Generate Chimeric Cynomolgus Monkeys. Cell Rep. Nov. 27, 2018;25(9):2563-2576.e9.
Lu et al., A defined xeno-free and feeder-free culture system for the derivation, expansion and direct differentiation of transgene-free patient-specific induced pluripotent stem cells. Biomaterials. Mar. 2014;35(9):2816.

(Continued)

*Primary Examiner* — Peter Paras, Jr.
*Assistant Examiner* — Khoa Nhat Tran
(74) *Attorney, Agent, or Firm* — Michael A. Whittaker

(57) ABSTRACT

The present invention relates to a method of expanding pluripotent stem cells (PSC) in suspension culture in a bioreactor, the method comprising (i) adding an inhibitor of ROCK (ROCKi) to pluripotent stem cells being cultivated in suspension in the bioreactor; (ii) adding a cell dissociation agent, thereby dissociating aggregates of the pluripotent stem cells; (iii) diluting the cell dissociation agent added in step (ii) by adding an excess volume of culture medium sufficient to decrease the concentration of the cell dissociation agent to a concentration at which cell aggregates can form again; and (iv) culturing of the mixture obtained in step (iii) under suitable conditions that allow the expansion of the PSCs.

23 Claims, 12 Drawing Sheets

(56) References Cited

OTHER PUBLICATIONS

Okita et al., A more efficient method to generate integration-free human iPS cells. Nat Methods. May 2011;8(5):409-411.
Takahashi and Yamanaka, Induction of pluripotent stem cells from mouse embryonic and adult fibroblast cultures by defined factors. Cell. Aug. 25, 2006;126(4):663-676.
Thomson et al., Embryonic stem cell lines derived from human blastocysts. Science. Nov. 6, 1998;282(5391):1145-1147.
Office Action issued by the CNIPA in Chinese Patent Application No. 202080085065.4 dated Mar. 21, 2024—incl Engl lang transl (14 pages total).
Office Action issued by the CNIPA in Chinese Patent Application No. 202080085065.4 dated Sep. 1, 2023—incl Engl lang transl (17 pages total).
Selvaraj et al., Screening identifies small molecules that enhance the maturation of human pluripotent stem cell-derived myotubes. Elife. Nov. 11, 2019:8:e47970.
Thermofisher, the home page: Culturing Pluripotent Stem Cells (PSCs) in Essential 8™ Medium. Technical Reference Library, (Sep. 27, 2015., and the WaybackMachine standard). Accessed online at: <https://www.thermofisher.com/kr/ko/home/references/protocols/cell-culture/ stem-cell-protocols/ipsc-protocols/culturing-puripotent-stem-cells-essential-8-medium.html> (6 pages total).
Office Action issued in related Korean patent application number 10-2022-7010856 dated Sep. 23, 2025—incl Engl lang transl (19 pages total).
European Communication pursuant to Article 94(3) EPC issued in EP20829814.1 on Dec. 19, 2025 (6 pages).
Le Minh Nguyen Tuyet et al: "Expansion Culture of Human Pluripotent Stem Cells and Production of Cardiomyocytes", Bioengineering, vol. 6, No. 2, May 24, 2019 (May 24, 2019).
Vincent C. Chen et al: "Scalable GMP compliant suspension culture system for human ES cells", Stem Cell Research, vol. 8, No. 3, May 1, 2012, pp. 388-402.
Olmer, Ruth, et al., "Suspension culture of human pluripotent stem cells in controlled, stirred bioreactors." Tissue Engineering Part C: Methods 18.10 (2012): 772-784.
Examination Report issued in IN 202217027999 on Jun. 2, 2026 (8 pages).

* cited by examiner

EXPANSION OF STEM CELLS IN SUSPENSION IN A BIOREACTOR

CROSS-REFERENCE TO RELATED APPLICATIONS

The present invention is filed under 35 U.S.C. § 371 as the U.S. national phase of International Application No. PCT/EP2020/085667, filed 11 Dec. 2020, which designated the U.S. and claims the benefit of priority of European Patent Application No. 19 215 091.0 filed 11 Dec. 2019, the contents of each of which is hereby incorporated by reference it its entirety for all purposes.

TECHNICAL FIELD OF THE INVENTION

The present invention relates to a method for expanding pluripotent stem cells (PSC) in suspension culture in a bioreactor.

BACKGROUND

Pluripotent stem cells (PSCs) are adherent cells and therefore usually cultivated in cell culture containers such as flasks, in which they adhere to the bottom of the container. To facilitate adherence, the bottom of the container is usually coated with proteins of the extracellular matrix (ECM). This cell culture method is however not useful for the production of high numbers of PSCs that are needed in clinical applications since the cultivation in cell culture flasks is time-consuming, labor-intensive and requires a significant amount of materials (culture medium and plastic ware). Suspension culture in stirring tank bioreactors has been described as an alternative to adherent culture. Here, the PSCs do not grow in single cell layers on the bottom of the cell culture container but form aggregates, in which the cells are attached to each other. There thus is no need for supplementation of ECM proteins in suspension culture to allow the formation of cell aggregates. Suspension culture is considered to be more efficient because the culture conditions can be controlled also for higher cell numbers and less material and time is needed.

The continuous proliferation of the PSCs in suspension culture however leads to a continuous increase of the size of the aggregates. Above a certain aggregate diameter, the cells inside the aggregate are no longer sufficiently supplied with nutrients and/or growth factors or other signal molecules, whereupon they spontaneously differentiate or become apoptotic. For a continuous expansion of the PSCs, the aggregates therefore have to be dissociated and the resulting single cells have to be reseeded ("passaged"). Passaging in the suspension culture however poses several problems: The dissociation of the aggregates can lead to a reduction in the viability of the PSCs or to spontaneous differentiation, as these are sensitive to external influences. In addition, it is difficult to automate this step in a closed system when a large number of cells are present because the cell medium must be quickly separated from the aggregates.

The method most often used for dissociation of aggregation is enzymatic digestion. Here, the adhesion molecules of the PSCs are cleaved proteolytically. Thereby, the cells are separated from each other. The use of enzymes or solutions comprising enzymes including Accutase, Accumax, trypsin, TrypLE Select and collagenase B has been described. The enzymatic reaction has to be stopped to prevent an overdigestion, which would again lead to lysis or apoptosis. Stopping of the enzymatic reagents is usually achieved by strong dilution or addition of a stop reagent followed by removal using centrifugation. In addition, enzymatic digestion influences the proliferation and aggregate formation of PSCs because membrane-bound adhesion molecules are removed in the process and must be formed again. Furthermore, the PSCs are often completely isolated from each other, which may negatively influence their pluripotency and viability.

Mechanical dissociation of cell aggregates has also been described in the art. Here, the aggregates are, e.g., forced through a sieve with a pore size that allows fragmentation in smaller aggregates. Often, the aggregates are pretreated with dissociation reagents. Again, this method poses environmental stress to the PSCs, which can then become apoptotic or start differentiation.

The enzymatic dissociation as well as the mechanical dissociation is usually carried out manually to allow the control and surveillance of the complete process. Additionally, the aggregates or cells are typically separated from the cell culture medium or dissociation reagent by centrifugation, which might lead to cell "clumping". Both should in particular be avoided in a GMP manufacturing process for the generation of therapeutic products—not only because it is labor-intensive and therefore expensive but also because each manual unit operation will increase the risk of microbial contamination and lot-to-lot variations.

Accordingly, there still is a need for cell dissociation or passaging methods that allow expansion of PSCs in a closed system, in which the entire process of dissociation and re-formation of PSC aggregates can be repeatedly performed without removing the cells or aggregates from the system and without exposing the cells to the stress that is associated with enzymatic/mechanic digestion and/or centrifugation. The technical problem therefore is to comply with this need.

SUMMARY OF THE INVENTION

The technical problem is solved by the subject-matter as defined in the claims. It is presented herein a method of expanding pluripotent stem cells (PSC) in suspension culture in a bioreactor.

Accordingly, the present invention relates to a method of expanding pluripotent stem cells (PSC) in suspension culture in a bioreactor, the method comprising

- (i) adding an inhibitor of ROCK (ROCKi) to pluripotent stem cells being cultivated in suspension in the bioreactor;
- (ii) adding a cell dissociation agent, thereby dissociating aggregates of the pluripotent stem cells;
- (iii) diluting the cell dissociation agent added in step (ii) by adding an excess volume of culture medium sufficient to decrease the concentration of the cell dissociation agent to a concentration at which cell aggregates can form again; and
- (iv) culturing of the mixture obtained in step (iii) under suitable conditions that allow the expansion of the PSCs.

The cell dissociation reagent preferably is a chelating agent, preferably the chelating agent is selected from the group consisting of ethylenediaminetetraacetate (EDTA), ethylene glycol-bis(β-aminoethyl ether)-N,N,N',N'-tetraacetic acid (EGTA), iminodisuccinic acid (IDS), polyaspartic acid, ethylenediamine-N,N'-disuccinic acid (EDDS), citrate, citric acid, 1,2-bis(o-aminophenoxy)ethane-N,N,N', N'-tetraacetic acid (BAPTA), and methylglycinediacetic acid (MGDA).

Preferably, the cell dissociation reagent is selected from the group consisting of EDTA, citrate, citric acid or combinations thereof.

Preferably, the final concentration of the cell dissociation agent such as EDTA, citric acid or citrate in step (ii) is at least 100 μM, in a range of about 100 to about 1000 μM in a range of about 250 to about 750 μM, in a range of about 400 to about 600 μM or is about 500 μM, preferably about 500 μM EDTA, citric acid or citrate.

Preferably, the concentration of the cell dissociation agent such as EDTA, citric acid or citrate in step (iii) after adding the excess volume of culture medium is about 100 μM or less, about 95 μM or less, about 90 μM or less, about 80 μM or less, about 70 μM or less, in a range of about 100 to about 1 μM EDTA, citric acid or citrate or in a range of about 90 to about 1 μM EDTA, citric acid or citrate.

Preferably, the excess volume exceeds the volume of the cell dissociation agent by at least 5 times. The cell dissociation preferably is stopped and re-formation of aggregates is initiated by adding an excess volume of at least 5 times.

Preferably, the culture medium in (iii) comprises a ROCKi.

Preferably, the method further comprises: (v) exchanging the medium to a medium essentially free of the ROCKi.

Preferably, step (iv) is performed for about 1 to about 3 days, preferably about 2 days.

Preferably, step (v) starts about 1 to about 3 days, preferably about 2 days, after step (iii).

Preferably, the ROCKi is selected from the group consisting of AS1892802, fasudil hydrochloride, GSK 269962, GSK 429286, H 1152, HA 1100, OXA 06, RKI 1447, SB 772077B, SR 3677, TC-S 7001, thiazovivin, Y27632 and combinations thereof. Preferably, the ROCKi is Y27632. Preferably, Y27632 is added to a final concentration of about 10 μM.

Preferably, the ROCKi is added in step (i) about 2 to about 4 hours prior to step (ii).

Preferably, the addition of an excess volume of the culture medium in step (iii) results in a cell number of about $1\times10^5$ to about $1\times10^6$ cells/ml, about 1.5 to about $7.5\times10^5$ cells/ml, about $2\times10^5$ to about $5\times10^5$ cells/ml, about $2\times10^5$ to about $3\times10^5$ cells/ml or about $2.5\times10^5$ cells/ml in the culture medium.

Preferably, the culture medium is selected from the group consisting of IPS-Brew, E8, StemFlex, mTeSR1, and PluriSTEM. Preferably, the culture medium is iPSC-Brew.

Preferably, the culture medium in steps (i) and (iii) is essentially identical.

Preferably, the temperature of the culture medium is about 30 to 50° C., about 35 to 40° C., about 36 to 38° C. or about 37° C., preferably 37° C.

Preferably, steps (i) to (iv) or (i) to (v) are repeated once, twice, 3 times, 4 times, 5 times, at least 5 times, or at least 10 times.

Preferably, the PSCs maintain their pluripotency after each repetition of steps (i) to (iv) or (v).

Preferably, the pluripotent stem cells are selected from the group consisting induced pluripotent stem cells (iPSC), embryonic stem cells (ESC), parthenogenetic stem cells (pPSC) and nuclear transfer derived PSCs (ntPSC). Most preferably, the pluripotent stem cells are iPSCs. In another more preferred embodiment, the pluripotent stem cells are ESC. In another more preferred embodiment, the pluripotent stem cells are parthenogenetic stem cells.

Preferably, the pluripotent stem cells are TC1133 cells.

Preferably, the aggregates in step (ii) have an average diameter of about 180 μm to about 250 μm, preferably about 200 μm to about 250 μm, most preferably about 200 μm.

Preferably, the aggregates are dissociated in step (ii) for at least about 1 min, at least about 2 min, at least about 3 min, at least about 5 min, at least about 10 min, for 1 to 20 min, for about 10 to about 20 min, for about 10 to about 15 min or for up to about 15 min, preferably for about 15 min.

BRIEF DESCRIPTION OF THE DRAWINGS

The invention will be better understood with reference to the detailed description when considered in conjunction with the non-limiting examples and the accompanying drawings, in which.

Figure 1:
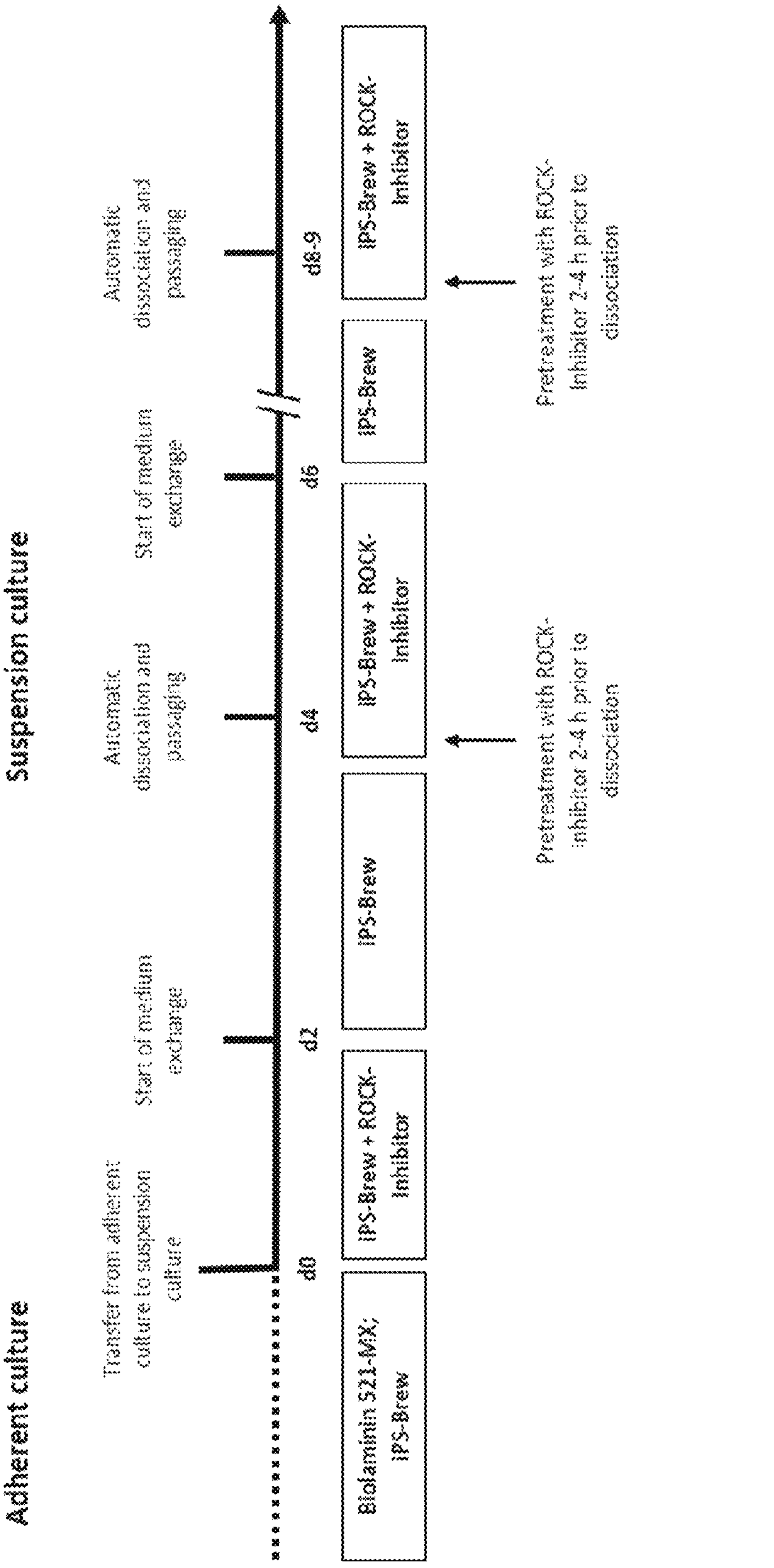
FIG. 1 shows an exemplary embodiment of the method of the invention. The method described with reference to FIG. 1 is also carried out in Examples 1 and 2. Here, the starter culture followed by two iterations or cycles of the passaging of the cells is shown. Prior to transfer to the suspension culture, PSCs such as iPSCs are cultured in standard cell culture flasks coated with Biolaminin 521-MX in IPS-Brew. For the start of the suspension culture, the PSCs are dissociated from the cell culture flask by addition of a cell dissociation agent, here Versene, and then used to inoculate the bioreactor, here at a seeding concentration of $2.5\times10^5$ cells/ml in a total volume of 13 ml. The cells are cultured for a period of about 2 days in a culture medium such as iPS-Brew supplemented with 10 μM ROCKi such as Y27632. After two days, the medium exchange to a culture medium such as iPS-Brew without the ROCKi is started. At day 4 or 5 when the aggregates preferably have grown in size to about 200-250 μm, the ROCKi, here 10 μM Y27632, is added for 2-4 hours (2 hours in Examples 1 and 2) prior to the dissociation step. This corresponds to step (i) of the method of the invention and may also be seen as the start of cycle 1 of the passaging of the cells. One cycle may comprise of steps (i) to (iv) and optionally also step (v) of the method of the invention.

Then, (automatic) dissociation (step (ii) of the method of the invention)) is carried out: Examples 1 and 2 provide such an exemplary method for the dissociation: First, the cells are washed two times with Versene, which includes stopping of stirring for about two minutes, removal of medium to about 2 ml, addition of Versene to 10 ml and starting the stirring (300 rpm, downwards) for 10 seconds. The stirring is again stopped for about 2 minutes, the medium removed to 2 ml and 3 ml Versene are added. Then the actual dissociation of the cell aggregates is performed by stirring at 600 rpm for up to 15 min until dissociation is complete. The cells may be counted. Then, the Versene solution is diluted by adding an excess volume of fresh iPS-Brew. This dilution corresponds to step (iii) of the method of the invention.

The passaged PSCs (concentration after dilution preferably is about $2\text{-}5\times10^5$ cells/ml) are then cultured in a culture medium such as iPS-Brew supplemented with 10 μM ROCKi such as Y27632 for two days until day 6 (step (iv) of the method of the invention). At day 6, the medium exchange to a culture medium such as IPS-Brew not supplemented with the ROCKi is started (optional step (v) of the method of the invention). This may be seen as the end of cycle 1 of the passaging cells.

At day 8-9, the next iteration (cycle 2) of the passaging of the cells starts: the ROCKi is added 2-4 hours prior to the dissociation step. This corresponds to step (i) of the method of the invention. Then, automatic dissociation (step (ii) of the method of the invention) and passaging (step (iii) of the method of the invention) is carried out. The passaged PSCs are then cultured in iPS-Brew supplemented with 10 μM ROCKi such as Y27632 for two days. Further steps of passaging and culturing can follow.

Figure 2:
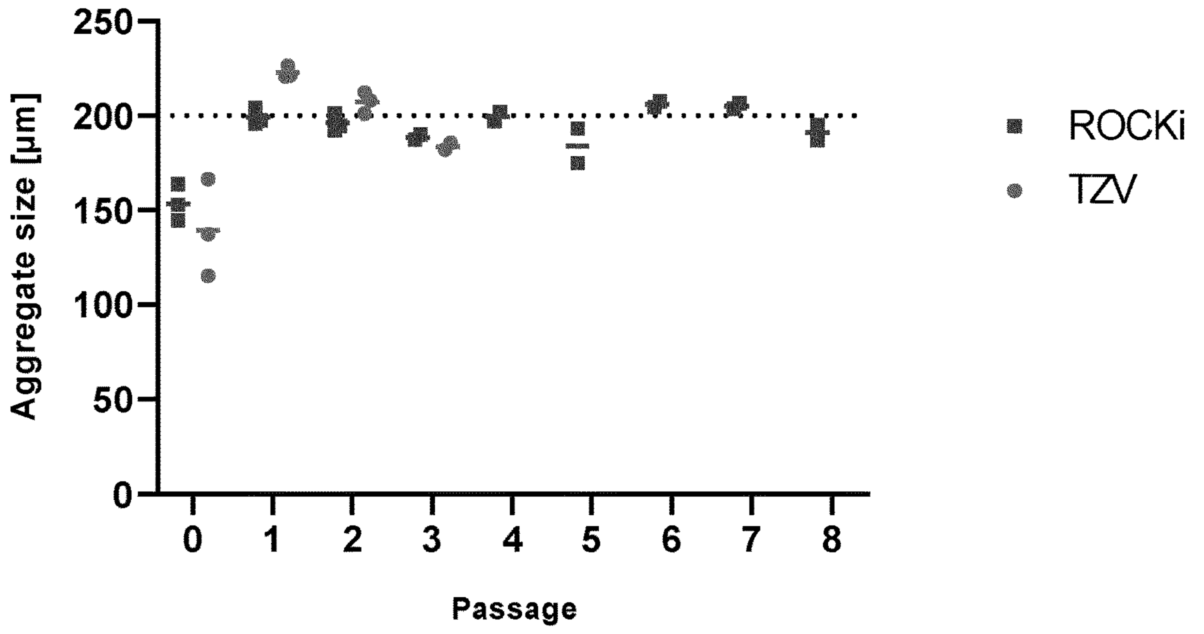

FIG. 2 shows the aggregate size at the last day of each passage obtained for the cultivation as carried out in Example 1 and as described for the exemplary embodiment of the method described with reference to FIG. 1. Individual data points represent values of single vessels. The mean value is represented by a line.

Figure 3:
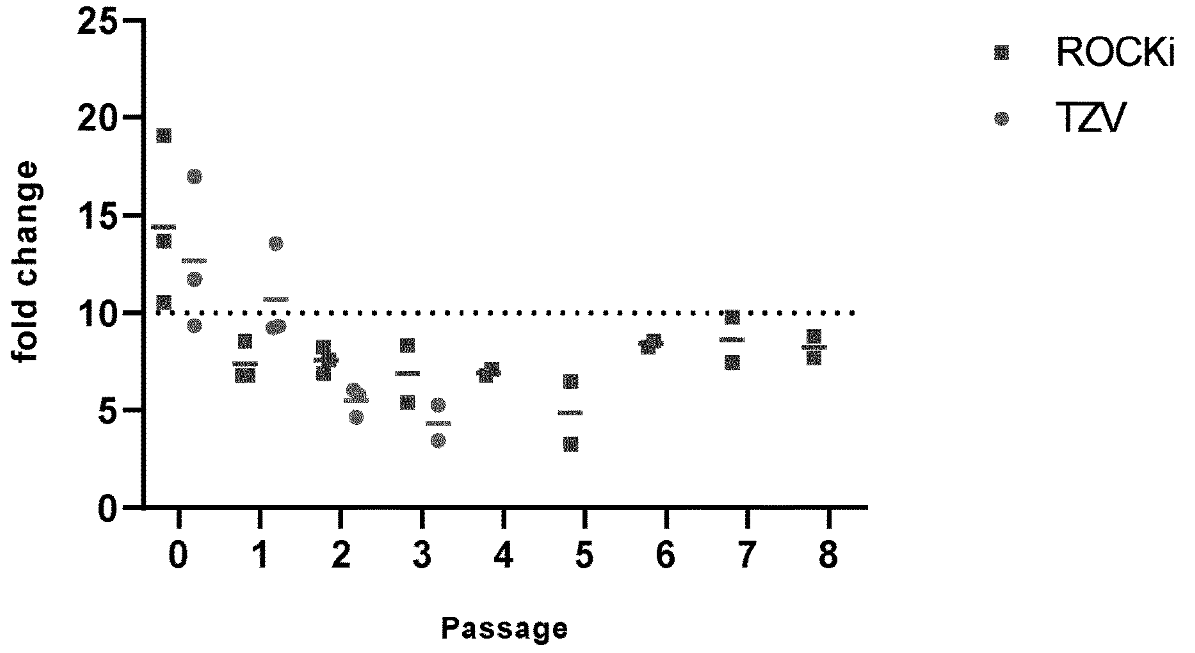

FIG. 3 shows the expansion rates of individual passages for the cultivation carried out in Example 1. Data points depict values of single vessels. Continuous lines represent the mean of the respective passage. Passages 6 and 8 lasted three days, whereas the other passages lasted 4-5 days.

Figure 4:
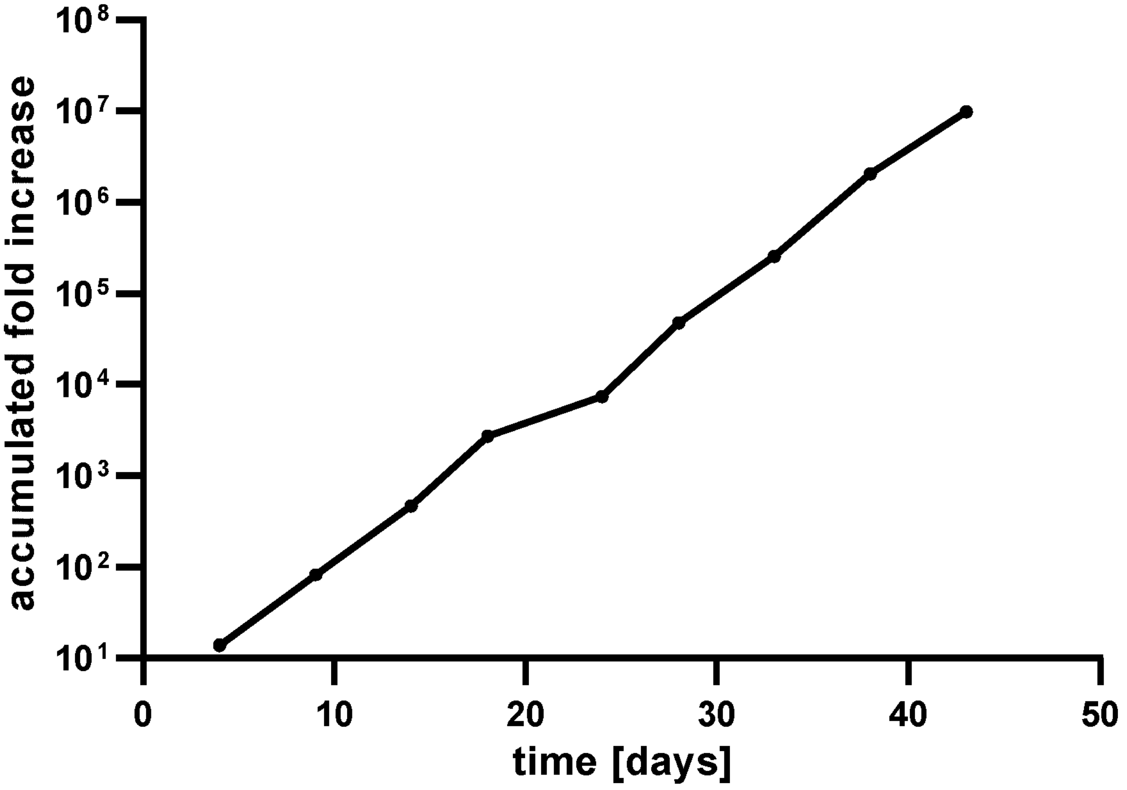

FIG. 4 shows the accumulated fold change during long-term suspension culture as carried out in Example 1. The accumulated fold change was calculated using the starting cell numbers during passaging and the respective splitting ratios.

Figure 5:
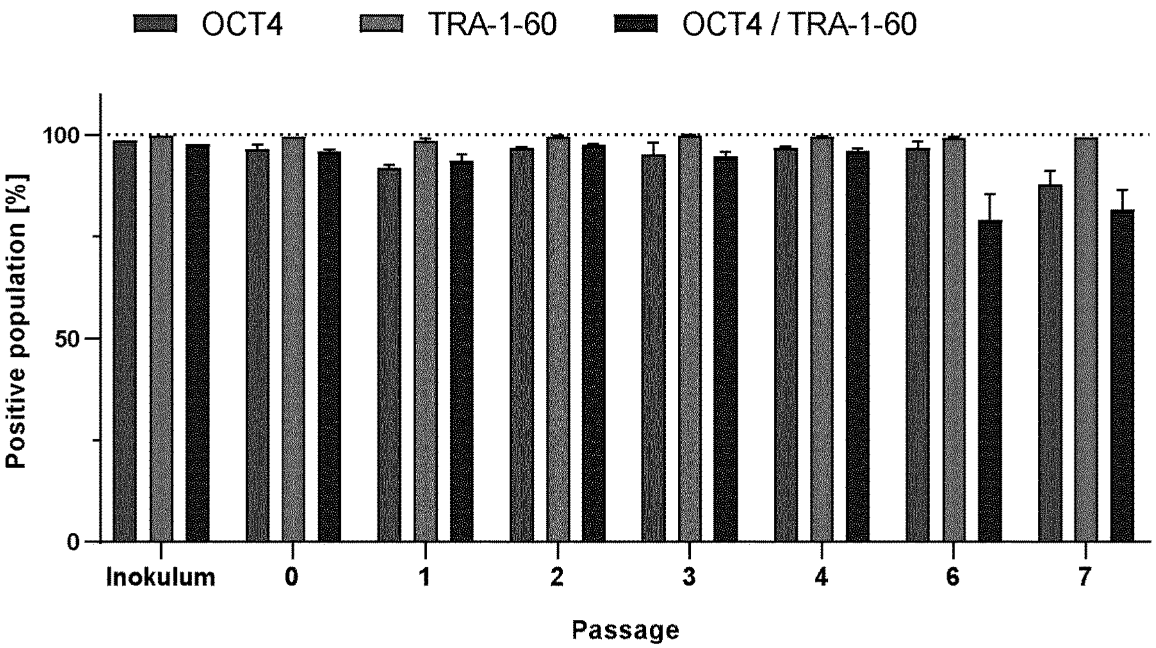

FIG. 5 shows the expression of pluripotency-related genes at the end of passages in ROCKi-treated iPSCs as carried out in Example 1: OCT4 (left), TRA-1-60 (middle) and OCT4/TRA-1-60 (right). Mean±SD.

Figure 6:
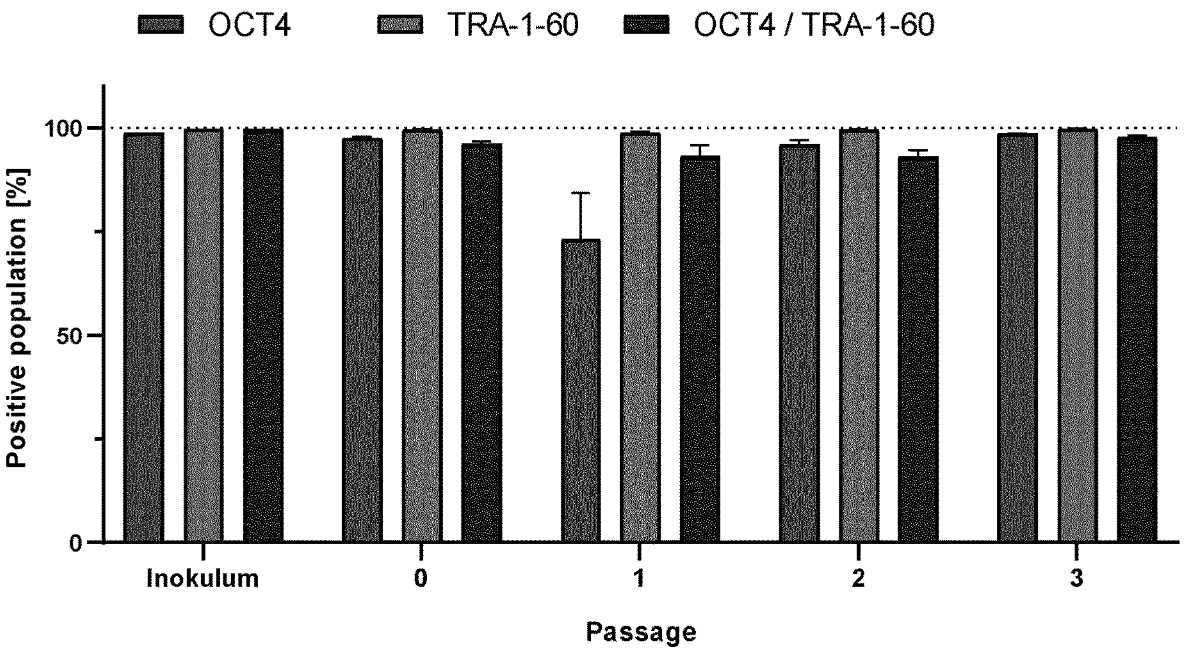

FIG. 6 shows the expression of pluripotency-related genes at the end of passages in TZV-treated iPSCs as carried out in Example 1: OCT4 (left), TRA-1-60 (middle) and OCT4/TRA-1-60 (right). Mean±SD.

Figure 7:
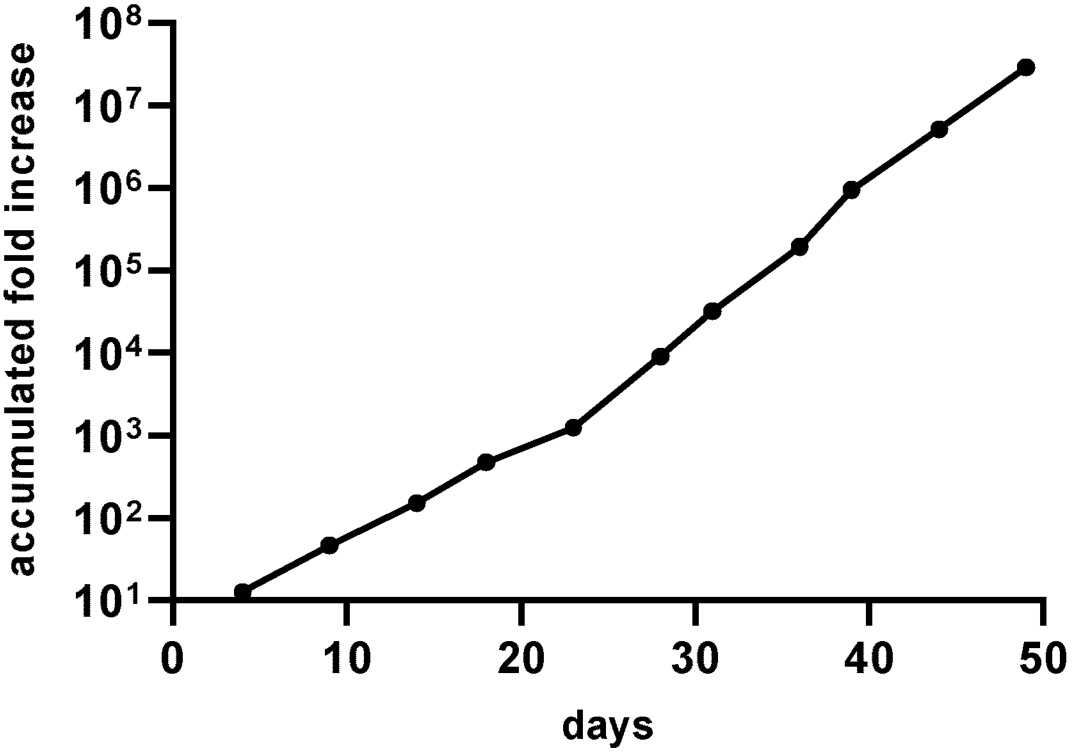

FIG. 7 shows the accumulated fold change during long-term suspension culture as carried out in Example 2. The accumulated fold change was calculated using the starting cell numbers during passaging and the respective splitting ratios.

Figure 8:
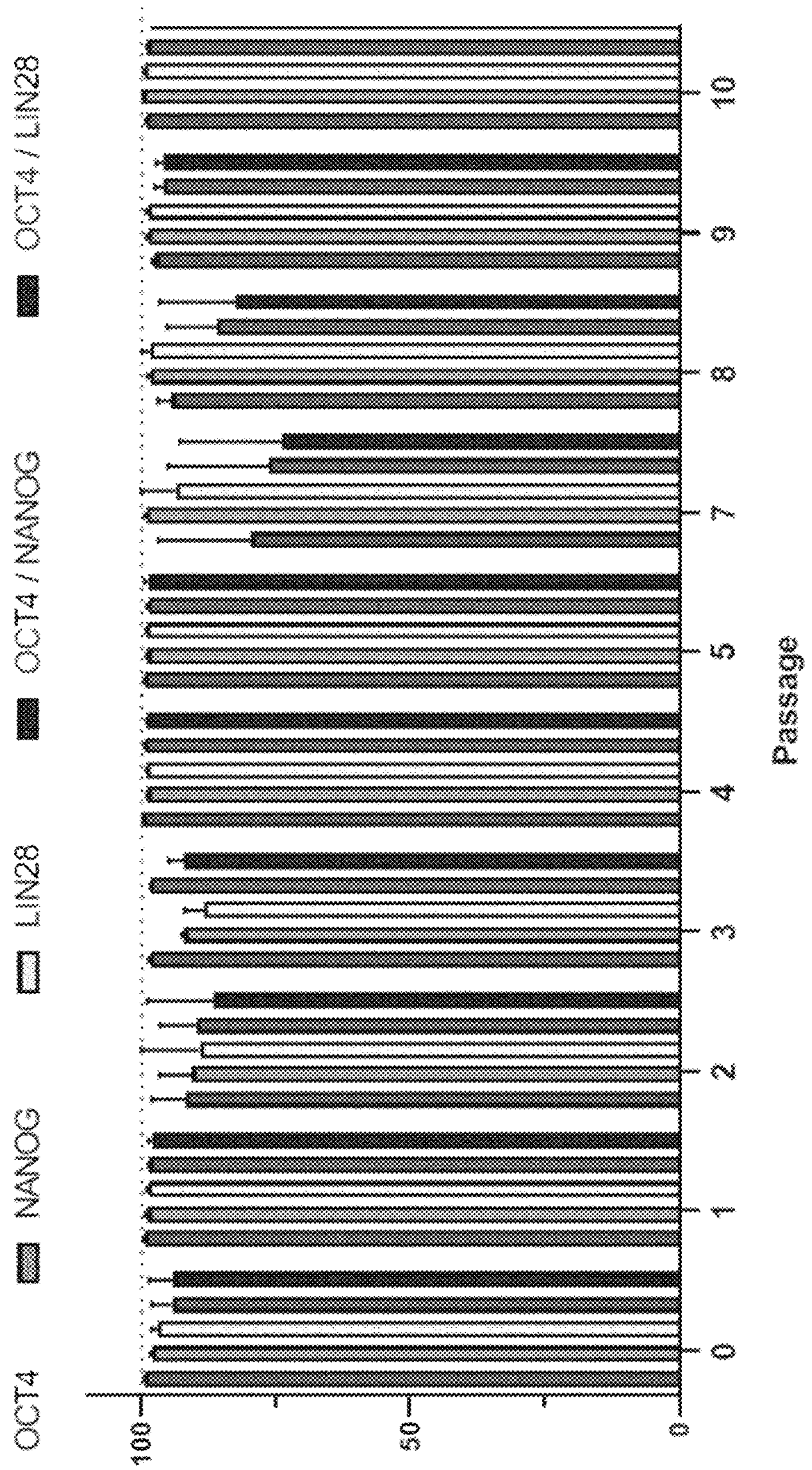

FIG. 8 shows the expression of pluripotency-related genes at the end of passages as carried out in Example 2: OCT4 (left), NANOG (middle left), LIN28 (middle), OCT4/NANOG (middle right) and OCT4/LIN28 (right). Mean±SD.

Figure 9:
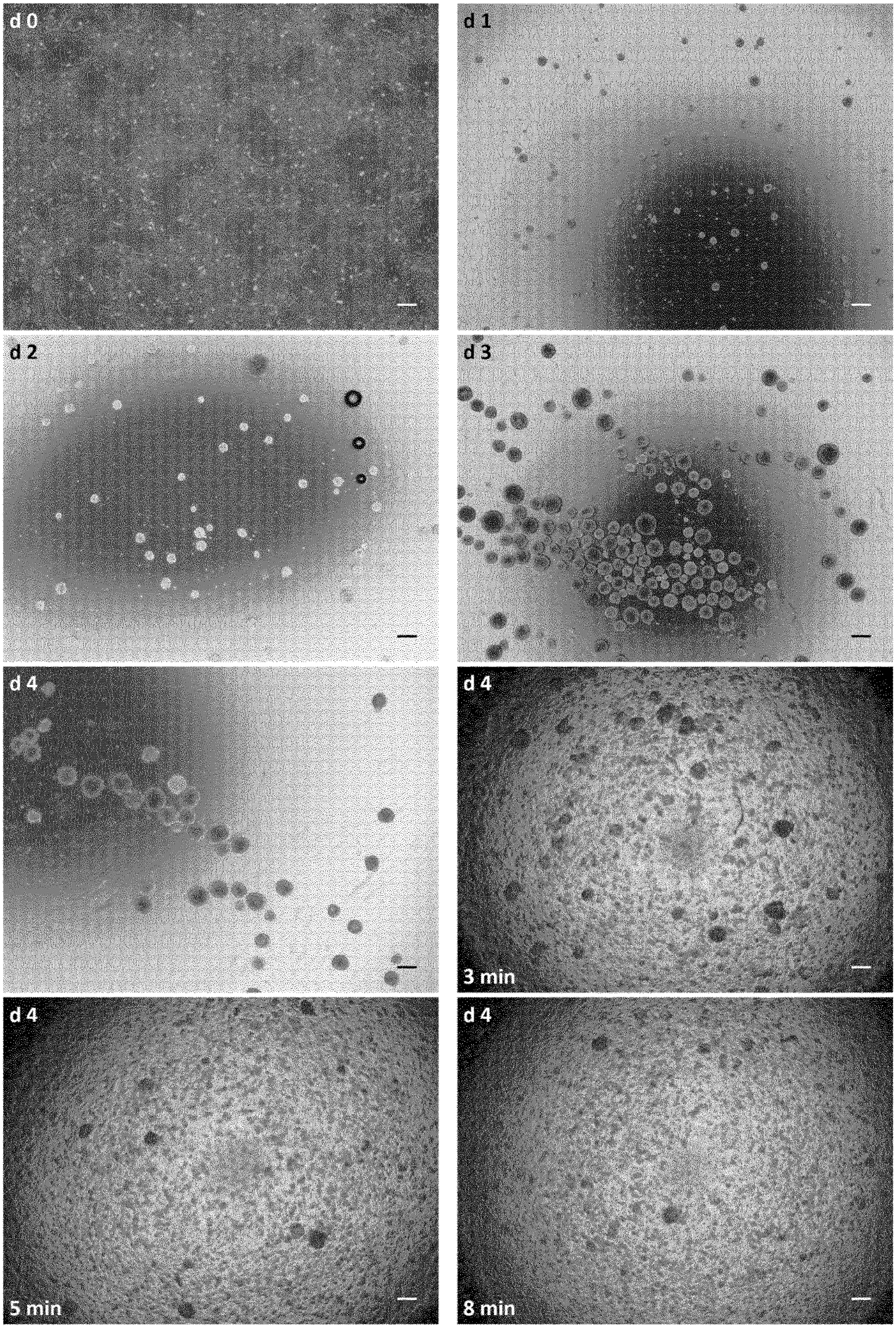

FIG. 9 shows the morphology of iPSCs. iPSCs were transferred from adherent culture (d 0) to suspension cell culture (d 1-4) as carried out in Example 3. At day 4 the aggregates were dissociated with Versene (d 4, 3-8 min) for passaging. Scale bars: 200 μm.

Figure 10:
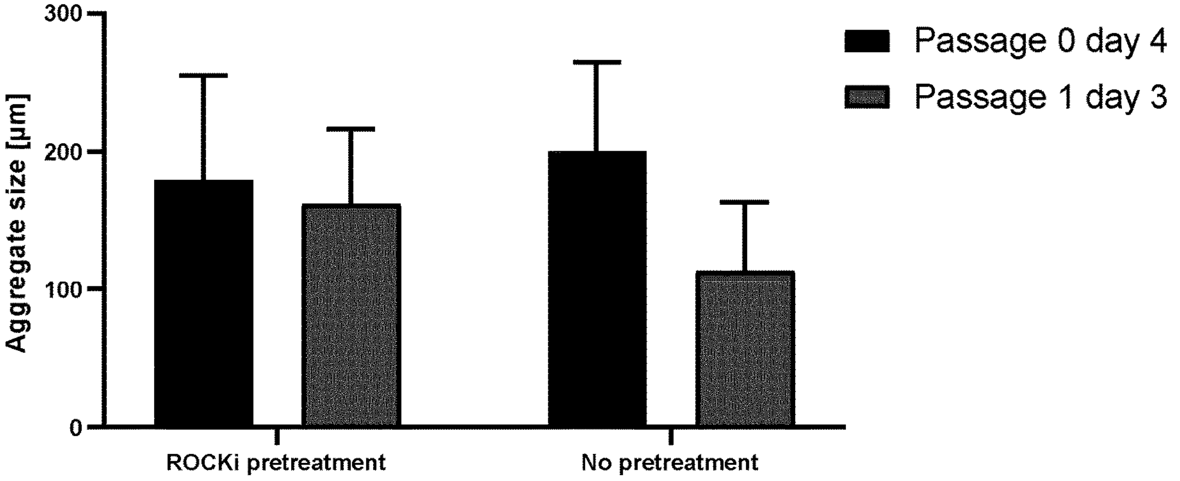

FIG. 10 shows the aggregate size of iPSCs with and without pretreatment before and after dissociating the cells as carried out in Example 4 at passage 0, day 4 (left bar) and at passage 1, day 3 (right bar).

Figure 11:
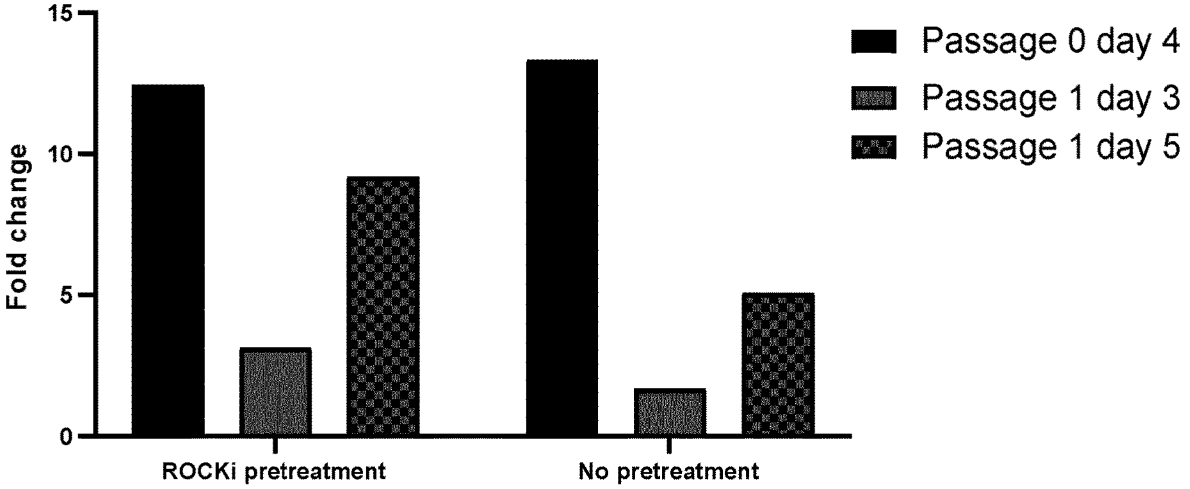

FIG. 11 shows the expansion rate of iPSCs (fold change) with and without pretreatment of ROCKi before and after dissociating the cells as carried out in Example 4 at passage 0, day 4 (left bar), at passage 1, day 3 (middle bar) and passage 1, day 5 (right bar).

Figure 12:
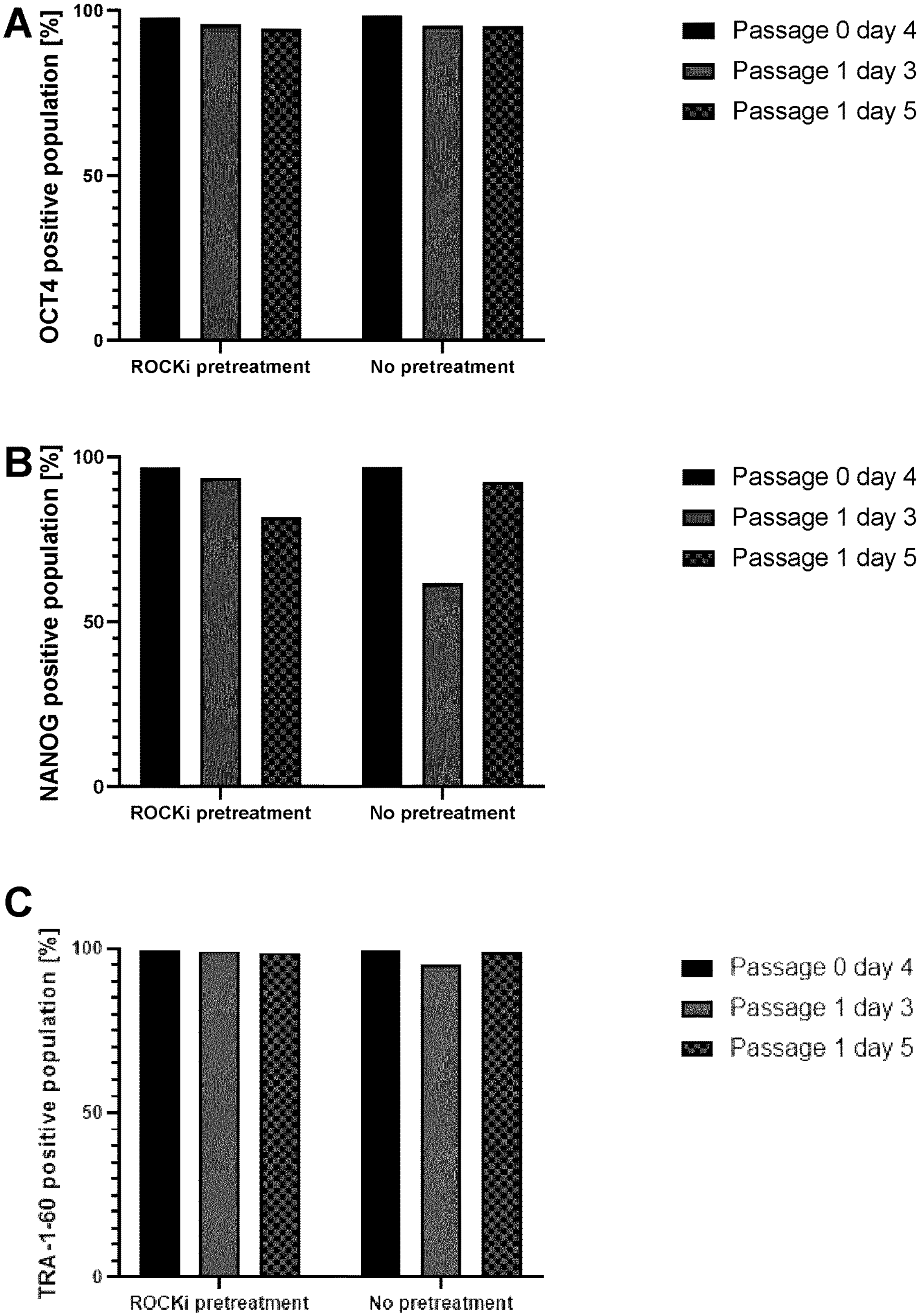

FIG. 12 shows the expression rate of pluripotency markers in iPSCs with and without pretreatment of ROCKi before and after dissociating the cells as carried out in Example 4 at passage 0, day 4 (left bar), at passage 1, day 3 (middle bar) and passage 1, day 5 (right bar). The pluripotency markers that were analyzed are OCT4 (FIG. 12A), NANOG (FIG. 12B) and TRA-1-60 (FIG. 12C).

Figure 13:
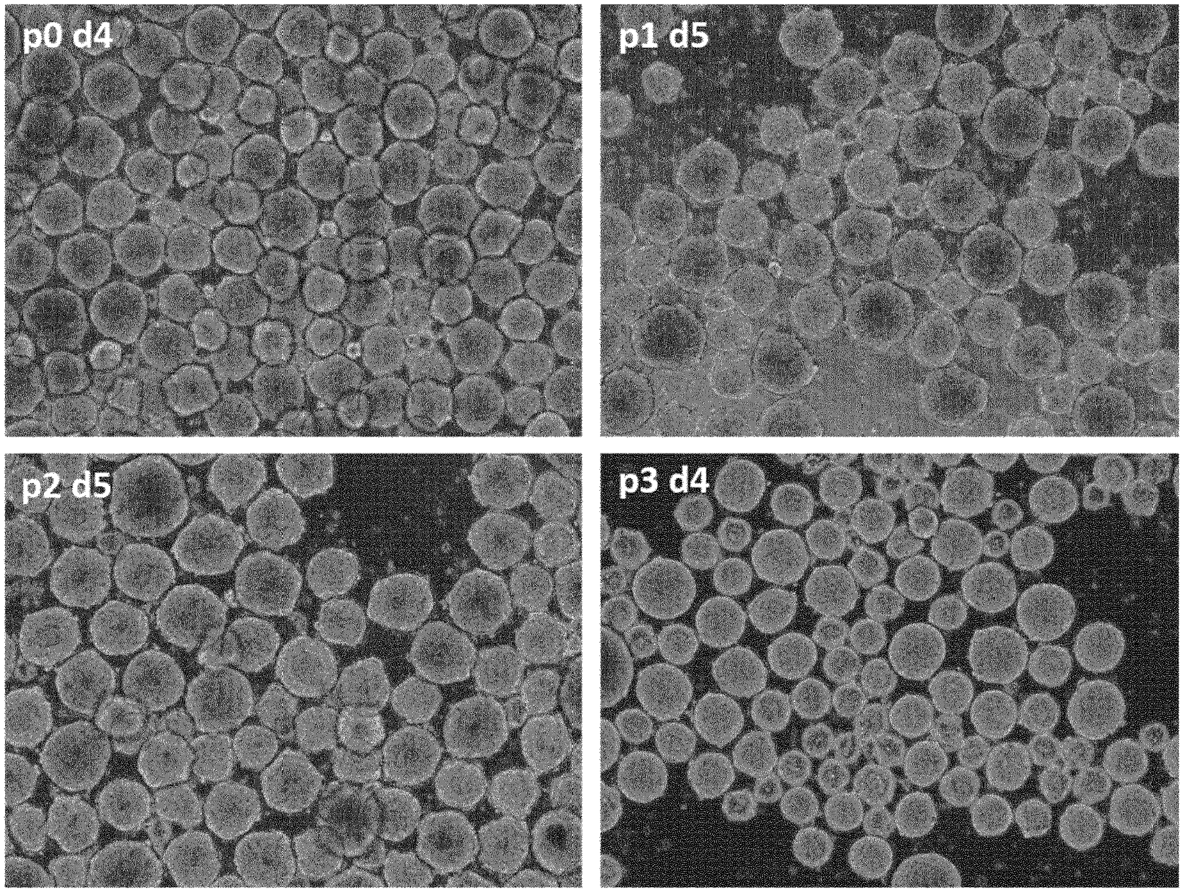

FIG. 13 shows the morphology of the cell aggregates at different time points (p0 day 4, p1 day 5, p2 day 5 and p3 day 4) at the end of each passage as carried out in Example 5.

Figure 14:
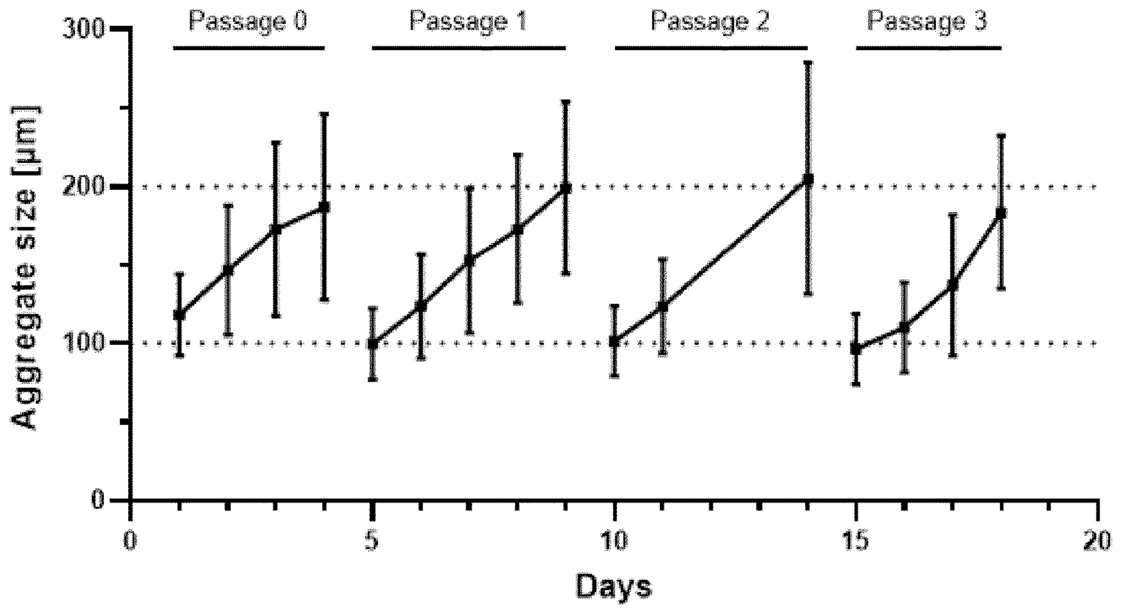

FIG. 14 shows the aggregate size during the different passages at each day of the cell expansion shown in Example 5.

Figure 15:
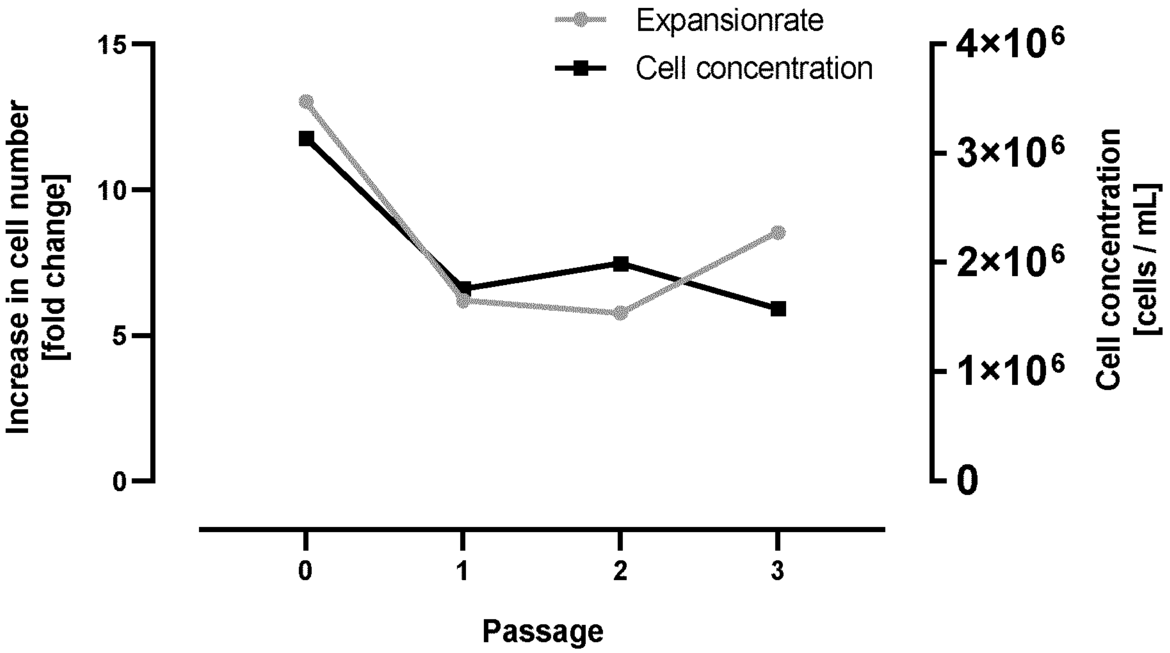

FIG. 15 shows the expansion rate (left axis, circles) and cell concentration (right axis, squares) at the end of all passages of Example 5.

Figure 16:
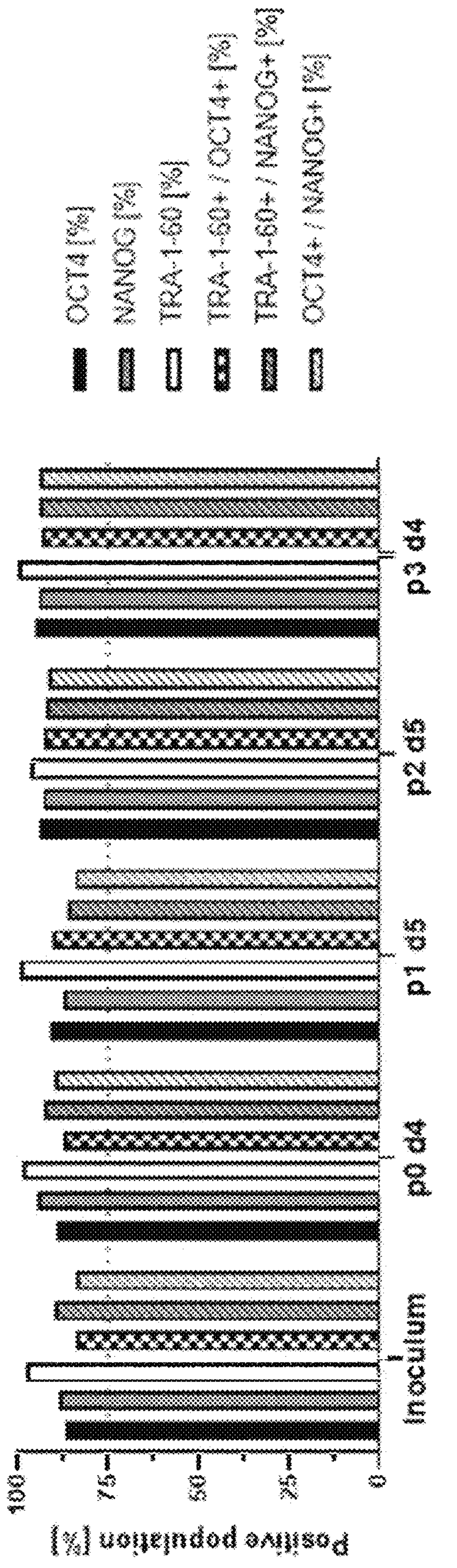

FIG. 16 shows the expression of pluripotency-related genes in iPSCs during at the shown time points of the different passages of Example 5.

DETAILED DESCRIPTION OF THE INVENTION

The present invention is described in detail in the following and will also be further illustrated by the appended examples and figures.

In the present invention it was successfully shown that it is possible to transfer PSCs from an adherent cell culture ("starter culture") to a continuous suspension culture in a bioreactor. It was surprisingly discovered that (a) the addition of an inhibitor of Rho-associated protein kinase (ROCK) prior to cell dissociation increases cell viability and yield and also helps maintaining the pluripotency of the PSCs (see e.g. Example 4) and (b) that PSCs can be cultured and expanded in a medium still comprising the cell dissociation reagent after diluting the cell dissociating reagent (see e.g. Examples 1, 2 and 3). Additionally, it was surprisingly found that (c) a chelating agent such as a solution comprising EDTA (ethylenediaminetetraacetate) can be used in dissociating aggregates of pluripotent stem cells (PSCs) (see Examples 1 and 2). Example 5 underlines that the present invention can be scaled up without further modifications by a factor of more than 30. The invention therefore allows for the automated cultivation of the PSCs in a closed system and thus reduces the number of manual operations such as the transfer of the PSCs out of the bioreactor into a centrifuge during the passaging of the cells. The method of the present invention thus is easier, faster and less expensive than conventional culture systems and allows further automatization of PSC production. Since the method of the invention can, as mentioned above, be carried out in a closed system, it has the further advantage that is ideally suited for establishing a GMP compliant manufacturing process for stem cells.

Before the continuous and automated expansion of PSCs in a bioreactor can be started, PSCs preferably have to be transferred to the bioreactor (see also FIG. 1). It is within the knowledge of a person skilled in the art to culture PSCs in adherent culture. E.g., PSCs may be cultured in T25/T75 culture flasks coated with 0.9 μg/cm$^2$ biolaminin 521-MX or other proteins of the ECM in a culture medium suitable for PSCs such as iPSC-Brew medium. For the start of the suspension culture, PSCs from adherent culture may be used. The cell may be dissociated from the flasks by a cell dissociation agent such as EDTA and transferred to the culture medium comprising a ROCKi. Preferably, cell aggregates consisting of 2 to 10 cells are present. These dissociated PSCs may then be used to inoculate a bioreactor. A preferred cell concentration at the beginning of the method of the invention is about 2.5×10$^5$ cells/ml. The cells are then cultured in suspension under continuous agitation to avoid sedimentation and/or adherence to the bottom of the bioreactor of the PSCs.

After inoculation, the cells preferably are cultured in the cell culture medium comprising the ROCKi for about 2 days to allow formation of cell aggregates. After formation of cell aggregates, the medium may be changed to a cell culture medium essentially free of a ROCKi, or in other words, a cell culture medium that has not been supplemented or comprises a ROCKi.

If the cell density and/or the size of the cell aggregate do no longer allow a suitable supply with nutrients (e.g., at a diameter of about 180 to 250 μm, preferably 200 μm), the PSCs may be passaged for the first time: First, a ROCKi is added to the culture medium, preferably 2 to 4 hours prior to dissociation of the aggregates. After pre-incubation of the cell aggregates in the cell culture medium comprising the ROCKi, the cells may be washed once or twice with a cell dissociation agent. Washing may include stopping the stirring of the cell aggregates in the bioreactor and allowing their sedimentation by gravity. Then, the culture medium or cell dissociation agent may be removed, preferably by aspiration, and replaced by (fresh) cell dissociation reagent. After addition, the cell aggregates may be stirred again, preferably for about 10 seconds at about 300 rpm, followed by another washing cycle. After two washing cycles with cell dissociation reagent, the PSCs can be kept in the cell dissociation reagent under continuous agitation, preferably at an increased stirring speed such as 600 rpm, until a suspension of smaller aggregates (about 5 to 50 cells) is formed. The dissociated PSCs may then be used to inoculate a further bioreactor by transferring a fraction of the cells to another bioreactor, where they are preferably diluted by addition of an excess volume of culture medium. Alternatively or additionally, the dissociated PSCs may be diluted in the same bioreactor, i.e. without the need of any cell transfer outside the closed system of the bioreactor. Alternatively or additionally, a fraction PSCs may be removed for clinical applications and the remaining PSCs may be used to inoculate the same bioreactor. The passaging is now completed. As outlined herein, the passaging may be repeated and thereby allows a continuous expansion of PSCs with a high yield at low costs. FIG. 1 shows an exemplary embodiment of the method of the invention including the starter culture.

Accordingly, the present invention relates to a method of expanding (induced) pluripotent stem cells (PSC) in suspension culture in a bioreactor, the method comprising (i) adding an inhibitor of ROCK (ROCKi) to pluripotent stem cells being cultivated in suspension in the bioreactor;
(ii) adding a cell dissociation agent, thereby dissociating aggregates of the pluripotent stem cells;
(iii) diluting the cell dissociation agent added in step (ii) by adding an excess volume of culture medium sufficient to decrease the concentration of the cell dissociation agent to a concentration at which cell aggregates can form again; and
(iv) culturing of the mixture obtained in step (iii) under suitable conditions that allow the expansion of the PSCs.

The method described herein may be seen as one iteration of passaging the PSCs in a continuous and/or automated process, preferably in a closed system such as a bioreactor. This passaging method reduces the number of manual operations that can lead to lot-to-lot variations or contaminations. As used herein, the terms "passage" and "passaging" refer to the process of sub-culturing adherent cells, in which cell adhesion is disrupted and the cell density (number of cells per unit volume or area) is reduced by addition of fresh medium. Accordingly, the present invention further relates to a method of passaging (induced) pluripotent stem cells (PSC) in suspension culture in a bioreactor, the method comprising (i) adding an inhibitor of ROCK (ROCKi) to pluripotent stem cells being cultivated in suspension in the bioreactor;

(ii) adding a cell dissociation agent, thereby dissociating aggregates of the pluripotent stem cells;
(iii) diluting the cell dissociation agent added in step (ii) by adding an excess volume of culture medium sufficient to decrease the concentration of the cell dissociation agent to a concentration at which cell aggregates can form again; and
(iv) culturing of the mixture obtained in step (iii) under suitable conditions that allow the expansion of the PSCs.

As outlined herein, the passaging of the PSCs may be repeated and therefore the method of the present invention allows a continuous process of expanding PSCs (expansion) in a cascade-like process. Accordingly, steps (i) to (iv) or (i) to (v) may be repeated once, twice, 3 times, 4 times, 5 times, at least 5 times, or at least 10 times. As shown in Examples 1 and 2 and FIGS. 5,6, and 8, the PSCs maintain their pluripotency after each repetition of steps (i) to (iv) or (v) of the method of the invention for an extended period of time, i.e. for at least 49 days and 10 passages as shown in Example 2. Therefore, the PSCs preferably maintain their pluripotency after each repetition of steps (i) to (iv) or (v).

The term "pluripotent stem cell" (PSC) as used herein refers to any cell that is able to differentiate into every cell type of the body. As such, pluripotent stem cells offer the unique opportunity to be differentiated into essentially any tissue or organ. Currently, the most utilized pluripotent cells are embryonic stem cells (ESC) or induced pluripotent stem cells (iPSC). Human ESC-lines were first established by Thomson and coworkers (Thomson et al. (1998), Science 282:1145-1147). Human ESC research recently enabled the development of a new technology to reprogram cells of the body into an ES-like cell. This technology was pioneered by Yamanaka and coworkers in 2006 (Takahashi & Yamanaka (2006), Cell, 126:663-676). Resulting induced pluripotent cells (iPSC) show a very similar behavior as ESC and, importantly, are also able to differentiate into every cell of the body. Another example of pluripotent stem cells that can be used in the present invention are parthenogenetic (PG) (embryonic) stem cells, which, can, for example in both mouse and human, be readily derived from blastocysts developing after in vitro activation of unfertilized oocytes (cf. in this context, for example Espejel et al, Parthenogenetic embryonic stem cells are an effective cell source for therapeutic liver repopulation, Stem Cells. 2014 July; 32(7): 1983-1988 or Didié et al, Parthenogenetic stem cells for tissue-engineered heart repair. J Clin Invest. 2013 March; 123(3):1285-98. Another example of suitable pluripotent stem cells that can be used herein are nuclear transfer derived PSCs (ntPSC; cf, Kang et al, Improving Cell Survival in Injected Embryos Allows Primed Pluripotent Stem Cells to Generate Chimeric Cynomolgus Monkeys, Cell Reports Volume 25, Issue 9, 27 Nov. 2018, Pages 2563-2576) In the context of the present invention, these pluripotent stem cells are however preferably not produced using a process which involves modifying the germ line genetic identity of human beings or which involves use of a human embryo for industrial or commercial purposes. Preferably, the pluripotent stem cells are of primate origin, including, but not limited to murine, rat, feline, canine, bovine, equine, simian or human origin, and more preferably are of human origin.

Suitable induced PSCs, can for example, be obtained from the NIH human embryonic stem cell registry, the European Bank of Induced Pluripotent Stem Cells (EBiSC), the Stem Cell Repository of the German Center for Cardiovascular Research (DZHK), or ATCC, to name only a few sources.

Induced pluripotent stem cells are also available for commercial use, for example, from the NINDS Human Sequence and Cell Repository (https://stemcells.nindsgenetics.org) which is operated by the U.S. National Institute of Neurological Disorders and Stroke (NINDS) and distributes human cell resources broadly to academic and industry researchers. One illustrative example of a suitable cell line that can be used in the present invention is the cell line TC-1133, an induced (unedited) pluripotent stem cell that has been derived from a cord blood stem cell. This cell line is, e.g. directly available from NINDS, USA. Preferably, TC-1133 is GMP-compliant. Further exemplary iPSC cell lines that can be used in the present invention, include but are not limited to, the Human Episomal iPSC Line of Gibco™ (order number A18945, Thermo Fisher Scientific), or the iPSC cell lines ATCC ACS-1004, ATCC ACS-1021, ATCC ACS-1025, ATCC ACS-1027 or ATCC ACS-1030 available from ATTC. Alternatively, any person skilled in the art of reprogramming can easily generate suitable iPSC lines by known protocols such as the one described by Okita et al, “A more efficient method to generate integration-free human iPS cells” Nature Methods, Vol. 8 No. 5, May 2011, pages 409-411 or by Lu et al “A defined xeno-free and feeder-free culture system for the derivation, expansion and direct differentiation of transgene-free patient-specific induced pluripotent stem cells”, Biomaterials 35 (2014) 2816e2826.

As explained herein, the (induced) pluripotent stem cell that is used in the present invention can be derived from any suitable cell type (for example, from a stem cell such as a mesenchymal stem cell, or an epithelial stem cell or a differentiated cells such as fibroblasts) and from any suitable source (bodily fluid or tissue). Examples of such sources (body fluids or tissue) include cord blood, skin, gingiva, urine, blood, bone marrow, any compartment of the umbilical cord (for example, the amniotic membrane of umbilical cord or Wharton’s jelly), the cord-placenta junction, placenta or adipose tissue, to name only a few. In one illustrative example, is the isolation of CD34-positive cells from umbilical cord blood for example by magnetic cell sorting using antibodies specifically directed against CD34 followed by reprogramming as described in Chou et al. (2011), Cell Research, 21:518-529. Baghbaderani et al. (2015), Stem Cell Reports, 5(4):647-659 show that the process of iPSC generation can be in compliance with the regulations of good manufacturing practice to generate cell line ND50039.

Accordingly, the pluripotent stem cell preferably fulfils the requirements of the good manufacturing practice.

The term “expanding” or “expansion of” PSCs or iPSCs as described herein describes an increase of cell number due to cell division. The method of the invention may further comprise a step of expanding the PSC. Cell expansion may occur in step (iv) of the method of the invention, in step (v) or in step (iv) of the method of the invention and (v) of the method of the invention, preferably in step (v) of the method of the invention. In one embodiment, step (iv) comprises culturing the mixture obtained in step (iii) under suitable conditions that allow the expansion of the PSCs, thereby expanding the PSC. In one embodiment, step (v) comprises exchanging the medium to a medium essentially free of the ROCKi, thereby expanding the PSC. Said step of expanding the PSC may relate to the time between addition of an inhibitor of ROCK (ROCKi) to pluripotent stem cells being cultivated in suspension in the bioreactor (see step (i) of the method of the invention) and diluting the cell dissociation agent added in step (ii) by adding an excess volume of culture medium sufficient to decrease the concentration of the cell dissociation agent to a concentration at which cell aggregates can form again (see step (iii) of the method of the invention), preferably lasts between about 2 and about 6 days, preferably about 3 and about 5 days, preferably about 3.5 to about 4.5 days, or more preferably about 4 days. “About” in this context may relate to a deviation of 8 hours or less, 4 hours or less, 2 hours or less or 1 hour or less.

The term “suspension culture” as used herein is a type of cell culture in which single cells or small aggregates of cells are allowed to function and multiply in an agitated growth medium, thus forming a suspension (c.f. the definition in chemistry: “small solid particles suspended in a liquid”). This is in contrast to adherent culture, in which the cells are attached to a cell culture container, which may be coated with proteins of the extracellular matrix (ECM). In suspension culture, preferably no proteins of the ECM are added to the cells and/or the culture medium.

As used herein, the terms “aggregate” and “cell aggregate”, which may be used interchangeably, refer to a plurality of (induced) pluripotent stem cells in which an association between the cells is caused by cell-cell interaction (e.g., by biologic attachments to one another). Biological attachment may be, for example, through surface proteins, such integrins, immunoglobulins, cadherins, selectins, or other cell adhesion molecules. For example, cells may spontaneously associate in suspension and form cell-cell attachments (e.g., self-assembly), thereby forming aggregates of the PSCs. In some embodiments, a cell aggregate may be substantially homogeneous (i.e., mostly containing cells of the same type). In some embodiments, a cell aggregate may be heterogeneous, (i.e., containing cells of more than one type).

In some embodiments, the aggregates have an average diameter of between about 150 and about 800 μm in size in step (ii) of the method of the invention. In some embodiments, the aggregates have an average diameter of at least about 800 μm in size in step (ii) of the method of the invention. In some embodiments, the aggregates have an average diameter of at least about 600 μm in size in step (ii) of the method of the invention. In some embodiments, the aggregates have an average diameter of at least about 500 μm in size in step (ii) of the method of the invention. In some embodiments, the aggregates have an average diameter of at least about 400 μm in size in step (ii) of the method of the invention. In some embodiments, the aggregates have an average diameter of at least about 300 μm in size in step (ii) of the method of the invention. In some embodiments, the aggregates have an average diameter of at least about 200 μm in size in step (ii) of the method of the invention. In some embodiments, the aggregates have an average diameter of at least about 150 μm in size in step (ii) of the method of the invention. In a preferred embodiment, the aggregates have an average diameter of between about 300 and about 500 μm in size in step (ii) of the method of the invention. In a preferred embodiment, the aggregates have an average diameter of between about 150 and about 300 μm in size in step (ii) of the method of the invention.

The formation of extensive PSC aggregate dimensions is preferably avoided since diameters exceeding about 300 μm may result in cell necrosis due to the limited nutrient and gas diffusion into the tissue/aggregate center. Eventually, uncontrolled differentiation—particularly in large PSC aggregates—might also occur. The regular dissociation of aggregates into single cells at every passage is therefore important. As shown in the Examples, the method of the present invention solves this problem in a convenient manner. In the present invention, it is shown that an average diameter of about 180 to about 250 μm before the cell aggregate dissociation, preferably about 200 to about 250 μm, ideally about 200 μm is the best compromise between pluripotency and yield of cells. Accordingly, the aggregates preferably have a diameter of about 180 to about 250 μm, more preferably about 200 to about 250 μm and most preferably of about 200 μm in size in step (ii) of the method of the invention.

As used herein, the terms “reactor” and “bioreactor”, which can be used interchangeably, refer to a closed culture vessel configured to provide a dynamic fluid environment for cell cultivation. Examples of agitated reactors include, but are not limited to, stirred tank bioreactors, wave-mixed/rocking bioreactors, up and down agitation bioreactors (i.e., agitation reactor comprising piston action), spinner flasks, shaker flasks, shaken bioreactors, paddle mixers, vertical wheel bioreactors. An agitated reactor may be configured to house a cell culture volume of between about 2 mL-20,000 L. Preferred bioreactors may have a volume of up to 50 L. An exemplary bioreactor suitable for the method of the present invention is the Ambr15® bioreactor or an UniVessel® bioreactor both of which are available from Sartorius Stedim Biotech (the latter is available in versions with 0.5 to 10 l volume, for example). The pH of the culture medium may be controlled by the bioreactor, preferably controlled by $CO_2$ supply, and may be held in a range of 6.6 to 7.6, preferably at about 7.4.

In some embodiments, the volume of the culture vessel in the bioreactor is from about 50 mL to about 20,000 L. In some embodiments, the volume of the culture vessel in the bioreactor is from about 50 mL to about 2,000 L. In some embodiments, the volume of the culture vessel in the bioreactor is from about 50 mL to about 200 L. In some embodiments, the volume of the culture vessel in the bioreactor is from about 50 mL to about 100 L. In some embodiments, the volume of the culture vessel in the bioreactor is from about 50 mL to about 50 L. In some embodiments, the volume of the culture vessel in the bioreactor is from about 50 mL to about 20 L. In some embodiments, the volume of the culture vessel in the bioreactor is from about 50 mL to about 10 L. In some embodiments, the volume of the culture vessel in the bioreactor is from about 50 mL to about 1 L. In some embodiments, the volume of the culture vessel in the bioreactor is from about 100 mL to about 10 L. In some embodiments, the volume of the culture vessel in the bioreactor is from about 100 mL to about 5 L. In some embodiments, the volume of the culture vessel in the bioreactor is from about 150 mL to about 1 L. In some embodiments, the volume of the culture vessel in the bioreactor is from about 1 L to about 1,000 L.

Especially preferred are bioreactors, in which the minimal and maximal cell culture volume differs by 5-fold or even 10-fold, i.e. bioreactors that can be understood to allow upscaling in the same bioreactor. Such a bioreactor may allow the start of PSC expansion in a relatively small volume, such as 200 mL. If the cell dissociation reagent is diluted by an excess volume of the culture medium, e.g. a 5-fold addition of cell culture medium, this yields a final volume of about 1 L after the first passage. After cell expansion, the cells are then separated again and the subsequent addition of an excess volume of culture medium then increases the volume to, e.g., 5 L after the second passage of the cells. Thus, in bioreactors that accept both relatively small and large volumes, the cells can be passaged in the same bioreactor several times without any manual operation (in a cascade-like process), e.g. removing a part of the cells and using this part to inoculate a further bioreactor while the remaining fraction of the cells is used to inoculate the bioreactor again (“repeated batch strategy” or “cascade-like process”). This allows the expansion of PSCs by around 1000-fold without any manual interaction such as transfer of cells in and out of the bioreactor necessary. This lack of manual interaction has the advantage of minimizing the risks of contamination and facilitates expansion of the PSCs under GMP conditions.

The method of the invention may be suitable for use at large-scale (e.g., between 1 l to 1000 l). In one preferred embodiment, for large scale production, the bioreactor suitable for use in the second or subsequent culture period(s) is a larger reactor than the bioreactor used for initial culture and dissociation. In one preferred embodiment, multiple bioreactors are inoculated in parallel for use in the second or subsequent culture period(s), thereby facilitating parallel serial passaging.

The bioreactor may be an agitated bioreactor or a stirring bioreactor. The speed of the stirrer preferably is optimized for each individual bioreactor. A person skilled in the art is capable of selecting a speed of the stirrer suitable for culturing of PSCs and dissociation of PSC cell aggregates. The speed of the stirrer for culturing of the PSCs preferably is lower such as in the range of about 150 to about 450 rpm, preferably about 300 rpm, in contrast to the speed suitable to facilitate cell dissociation, which might require a higher speed such as in the range of about 450 rpm to about 750 rpm, preferably about 600 rpm. For washing, the stirring speed preferably is in the range of about 150 to about 450 rpm, preferably about 300 rpm. Accordingly, in one embodiment the bioreactor is the ambr15 bioreactor of Sartorius Stedim and the stirring speed is 300 rpm for cell growth and 600 rpm for cell dissociation.

As used herein, the terms “dissociate” and “dissociation” refer to a process of separating aggregated cells from one another. For example, during dissociation, the cell-cell interaction between cells and between cells may be disrupted, thereby breaking apart the cells in the aggregate.

As used herein, the term “cell dissociation agent” or “cell dissociation reagent”—both of which can be used interchangeably—refer to a reagent or a solution comprising one or more reagents that separate cells from one another, such as, for example, chelating agent(s). For example, a dissociation reagent may break the bonds between cells, thereby disrupting the aggregation of cells in suspension. For example, the dissociation reagent may be a chelating agent, which may cause sequestration of a molecule to weaken or break bond formation between cell adhesion proteins, e.g. by chelation to disrupt calcium- or magnesium-dependent adhesion molecules.

Accordingly, the dissociation reagent preferably is a chelating agent. A “chelating reagent” as used herein may be a (organic) compound, peptide or protein that chelates divalent cations such as $Ca^{2+}$ or $Mg^{2+}$. Chelation is a type of bonding of ions and molecules to metal ions. It involves the formation or presence of two or more separate coordinate bonds between a polydentate (multiple bonded) ligand and a single central atom.

The chelating agent may be selected from the group consisting of ethylenediaminetetraacetate (EDTA), ethylene glycol-bis(β-aminoethyl ether)-N, N, N',N'-tetraacetic acid (EGTA), iminodisuccinic acid (IDS), polyaspartic acid, ethylenediamine-N,N'-disuccinic acid (EDDS), citrate, citric acid, 1,2-bis(o-aminophenoxy)ethane-N,N,N',N'-tetraacetic acid (BAPTA), and methylglycinediacetic acid (MGDA). The chelating agent may be ethylenediaminetetraacetate (EDTA). The chelating agent may be ethylene glycol-bis(β-aminoethyl ether)-N,N,N',N'-tetraacetic acid (EGTA). The chelating agent may be iminodisuccinic acid (IDS). The chelating agent may be polyaspartic acid. The chelating agent may be ethylenediamine-N,N'-disuccinic acid (EDDS). The chelating agent may be citrate. The chelating acid may be citric acid. The chelating agent may be 1,2-bis (o-aminophenoxy)ethane-N,N,N', N'-tetraacetic acid (BAPTA). The chelating agent may be methylglycinediacetic acid (MGDA). Preferably, the chelating agent is EDTA. The commercially available "Versene" solution comprising EDTA available from ThermoFisher Scientific is an exemplary and preferred dissociation reagent.

The final concentration of the chelating agent that is used in step (ii) may be at least 100 μM, in a range of about 100 to about 1000 μM, in a range of about 250 to about 750 μM, in a range of about 400 to about 600 μM or is about 500 μM, preferably about 500 μM. The final concentration of the chelating agent that is used in step (ii) may be at least 100 μM EDTA, in a range of about 100 to about 1000 μM EDTA, in a range of about 250 to about 750 μM EDTA, in a range of about 400 to about 600 μM EDTA or is about 500 μM EDTA, preferably about 500 μM EDTA.

As described herein, the use of proteolytic enzymes has a negative influence of cell viability and pluripotency of the PSCs and preferably is avoided. Accordingly, the cell dissociation agent preferably is essentially free of enzymes such as proteolytic enzymes. "Essentially free of enzymes" in this context can relate to a cell dissociation agent, to which no enzymes, preferably proteolytic enzymes such as trypsin, pepsin etc. have been added. Thus, "essentially free of enzymes" may exclude enzymes or solutions comprising enzymes including Accutase, Accumax, trypsin, TrypLE Select and collagenase B.

As used herein, the terms "dissociated" and "dissociated aggregate" refer to single cells, or cell aggregates or clusters that are smaller than the original cell aggregates (i.e., smaller than a pre-dissociation aggregate, e.g. as in step (i)). For example, a dissociated aggregate may comprise about 50% or less surface area, volume, or diameter relative to a pre-dissociation cell aggregate. The dissociated aggregate may consist of cell aggregates having 2 to 10 PSCs or having 1 to 10 PSCs. Preferably, the dissociated cell aggregates have a diameter of about 25 μm to about 130 μm, more preferably of about 80 μm to about 100 μm after step (iii) of the method of the invention.

The size of the resulting dissociated aggregates may be controlled by the amount of time, for which the cell dissociation reagent in step (ii) of the method of the invention is undiluted. Accordingly, the aggregates preferably are dissociated in step (ii) for at least about 1 min, at least about 2 min, at least about 3 min, at least about 5 min, at least about 10 min, for 1 to 20 min, for about 10 to about 20 min, for about 10 to about 15 min or for up to about 15 min, preferably for about 15 min.

As outlined herein, one advantage of the present invention is that the dissociation reagent not necessarily must be removed but that it is possible to further continue culturing of the PSCs without the need of a washing step, which e.g., including centrifugation or other mechanical manipulations of the cells. Thus, the PSCs are unharmed and can be cultured after dissociation in a medium still comprising the diluted dissociation reagent, thereby allowing the reformation of cell aggregates. Thereby error-prone and contamination-prone manual operations can be avoided, which is especially desired under GMP conditions. The dilution step (iii) of the method of the invention decreases the concentration of the cell dissociation agent to a concentration at which cell aggregates can form again, thereby stopping the cell dissociation reaction. In case the cell dissociation agent is a chelating agent, the excess volume of the added medium in step (iii) can provide a sufficient amount of ions to saturate the chelating agent so that the ions of the added culture medium can replace the ions bound by the chelating agent in step (ii). If EDTA is used as chelating agent, preferably with a (final) concentration of about 500 μM, the dissociation reagent added in step (ii) can be diluted by an excess of 5 volumes of culture medium. Preferably, the concentration of the dissociation agent after dilution in step (iii) in the resulting mixture is about 100 μM or less, about 95 μM or less, about 90 μM or less, about 80 μM or less, about 70 μM or less, in a range of about 100 to about 1 μM, or in a range of about 90 to about 1 μM. In case the dissociation reagent is EDTA, the concentration of the dissociation agent after dilution in step (iii) in the resulting mixture is about 100 μM or less EDTA, about 95 μM or less EDTA, about 90 μM or less EDTA, about 80 μM or less EDTA, about 70 μM or less EDTA, in a range of about 100 to about 1 μM EDTA, or in a range of about 90 to about 1 μM EDTA.

The term "excess volume" as used herein may relate to a volume that exceeds the amount of dissociation reagent added in step (ii) by at least 2-fold, at least 3-fold, at least 4-fold, at least 5-fold, at least 7.5-fold, at least 10-fold, at least 20-fold or at least 30-fold.

Rho-associated protein kinase (ROCK) is a kinase belonging to the AGC (PKA/PKG/PKC) family of serine-threonine kinases. It is involved mainly in regulating the shape and movement of cells by acting on the cytoskeleton. ROCKs (ROCK1 and ROCK2) occur in mammals (human, rat, mouse, cow), zebrafish, *Xenopus*, invertebrates (*C. elegans*, mosquito, *Drosophila*) and chicken. Human ROCK1 has a molecular mass of 158 kDa and is a major downstream effector of the small GTPase RhoA. Mammalian ROCK consists of a kinase domain, a coiled-coil region and a Pleckstrin homology (PH) domain, which reduces the kinase activity of ROCKs by an autoinhibitory intramolecular fold if RhoA-GTP is not present. ROCK1 is mainly expressed in the lung, liver, spleen, kidney and testis. However, ROCK2 is distributed mostly in the brain and heart. Protein kinase C and Rho-associated protein kinase are involved in regulating calcium ion intake; these calcium ions, in turn stimulate a myosin light chain kinase, forcing a contraction.

Inhibitors of ROCK (ROCKi) are well known to a person skilled in the art. Examples of ROCKi include, but are not limited to, AS1892802, fasudil hydrochloride, GSK 269962, GSK 429286, H 1152, HA 1100, OXA 06, RKI 1447, SB 772077B, SR 3677, TC-S 7001, thiazovivin and Y27632. Preferably, the ROCKi is Y27632. The concentration of the ROCKi, such as Y27632, preferably is in the range of 1 to 100 μM, 2 to 80 μM, 5 to 50 μM, 5 to 25 μM or about 10 μM. Y27632 has the following structure 1:

1

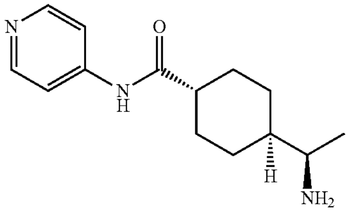

Preferably, the ROCKi is thiazovivin. The concentration of the ROCKi, such as thiazovivin, preferably is in the range of 1 to 100 μM, 2 to 80 μM, 5 to 50 μM, 5 to 25 μM or about 10 μM. Thiazovivin has the following structure 2:

2

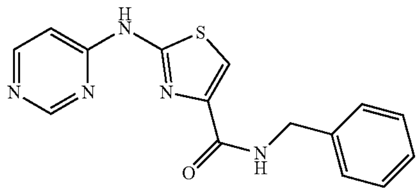

An inhibitor of ROCK may be added in the culture medium used in step (iii) in the method of the invention to facilitate cell survival and cell re-aggregation of the PSCs (see e.g. Example 4). Accordingly, the culture medium in step (iii) preferably comprises a ROCKi. Similarly, a ROCKi is added in step (i) of the method of the invention to the PSCs that are cultivated in a bioreactor. The addition of the ROCKi may be done about 2 hours to about 4 hours prior to step (ii) of the method of the invention.

Continuous administration of a ROCKi to PSCs suspension cultures after (re-)formation of aggregates might decrease the yield of the PSC culture. Thus, in one embodiment of the invention, the culture medium is changed to a medium essentially free of a ROCKi, preferably after the PSCs have formed aggregates again. Accordingly, the method of the present invention may further comprise step (v): exchanging the medium to a medium essentially free of the ROCKi. It may take up to 3 days until aggregates of the PSCs have been formed again in the suspension culture. Accordingly, the culture medium that is used after dilution step (iii) of the method of the invention preferably comprises a ROCKi for about 1 to about 3 days, preferably 2 days. In other words, step (iv) of the method of the invention is performed for about 1 to 3 days, preferably about 2 days. The exchange of the medium to a medium essentially free of the ROCKi may start for about 1 to 3 days, preferably about 2 days after step (iii) of the method of the invention, i.e. after dilution of the cell dissociation agent.

In one embodiment of the invention, the addition of an excess volume of the culture medium in step (iii) results in a cell number of about $1\times10^5$ to about $1\times10^6$ cells/ml, about 1.5 to about $7.5\times10^5$ cells/ml, about $2\times10^5$ to about $5\times10^5$ cells/ml, about $2\times10^5$ to about $3\times10^5$ cells/ml or about $2.5\times10^5$ cells/ml in the culture medium.

The PSCs cultured in suspension in the bioreactor are cultured in a culture medium. Culture media that allow the expansion of the PSCs are known to a person skilled in the art and include, but are not limited to, IPS-Brew, iPS-Brew XF, E8, StemFlex, mTeSR1, PluriSTEM, StemMACS, TeSRTM2, Corning NutriStem hPSC XF Medium, Essential 8 Medium (ThermoFisher Scientific), StemFit Basic02 (Ajinomoto Co. Inc), to name only a few. In one illustrative example, the culture medium is IPS-Brew that is available in GMP grade from Miltenyi Biotec, Germany. The culture medium, in which the cells are cultured prior to addition of the ROCKi in step (i) of the method of the invention, may be the same, which is used to dilute the cell dissociation agent in step (iii) of the method of the invention. Accordingly, the culture medium in steps (i) and (iii) of the method of the invention may be essentially identical. The culture medium used in steps (iv) and (v) may also be identical to the culture medium used in steps (i) and (iii) of the method of the invention.

The culture medium may be continuously exchanged using perfusion in the method of the invention. Perfusion is characterized by the continuous replacement of medium from the reactor by fresh medium while retaining cells in the vessel by specific systems (see also the review article of Kropp et al. "Progress and challenges in large-scale expansion of human pluripotent stem cells" Process Biochemistry, Vol. 59, Part B, August 2017, Pages 244-254). Perfusion is an operation mode for biopharmaceutical production processes enabling highest cell densities and productivity. Beside the advantage that cells in perfusion are constantly provided with fresh nutrients and growth factors, potentially toxic waste products are washed out, ensuring more homogeneous conditions in the reactor. Moreover, compared to repeated batch processes, perfusion processes support process automation and improved feedback control of the culture environment, including DO, pH, and nutrient concentrations. Perfusion cultures may enable a relatively stable, physiological environment that also supports the self-conditioning ability of PSCs by their endogenous factor secretion and thus eventually reducing supplementation of expensive medium components. The culture medium may accordingly be continuously exchanged by perfusion in step (iv). The culture medium may be continuously exchanged by perfusion in step (v). The culture medium may be continuously exchanged by perfusion in steps (iv) and (v). Continuous medium exchange by perfusion with a culture medium being essentially free of the ROCKi can be used in step (iv) to exchange the medium to a medium essentially free of the ROCKi. Thus, in one embodiment, step (iv) of the method of the invention comprises: culturing of the mixture obtained in step (iii) under suitable conditions that allow the expansion of the PSCs, wherein the culture medium is exchanged by perfusion with a medium essentially free of the ROCKi.

Another condition that determines whether the conditions are suitable for the expansion of the PSCs includes temperature. Accordingly, wherein the temperature of the culture medium is about 30 to 50° C., about 35 to 40° C., about 36 to 38° C. or about 37° C., preferably 37° C.

It is noted that as used herein, the singular forms "a", "an", and "the", include plural references unless the context clearly indicates otherwise. Thus, for example, reference to "a reagent" includes one or more of such different reagents and reference to "the method" includes reference to equivalent steps and methods known to those of ordinary skill in the art that could be modified or substituted for the methods described herein.

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the present invention.

The term "and/or" wherever used herein includes the meaning of "and", "or" and "all or any other combination of the elements connected by said term".

The term "less than" or in turn "more than" does not include the concrete number.

For example, less than 20 means less than the number indicated. Similarly, more than or greater than means more than or greater than the indicated number, e.g. more than 80% means more than or greater than the indicated number of 80%.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. When used herein the term "comprising" can be substituted with the term "containing" or "including" or sometimes when used herein with the term "having". When used herein "consisting of" excludes any element, step, or ingredient not specified.

The term "including" means "including but not limited to". "Including" and "including but not limited to" are used interchangeably.

As used herein the term "about" or "approximately" means within 20%, preferably within 15%, preferably within 10%, and more preferably within 5% of a given value or range. It also includes the concrete number, i.e. "about 20" includes the number of 20.

It should be understood that this invention is not limited to the particular methodology, protocols, material, reagents, and substances, etc., described herein and as such can vary. The terminology used herein is for the purpose of describing particular embodiments only, and is not intended to limit the scope of the present invention, which is defined solely by the claims.

All publications cited throughout the text of this specification (including all patents, patent application, scientific publications, instructions, etc.), whether supra or infra, are hereby incorporated by reference in their entirety. Nothing herein is to be construed as an admission that the invention is not entitled to antedate such disclosure by virtue of prior invention. To the extent the material incorporated by reference contradicts or is inconsistent with this specification, the specification will supersede any such material.

The content of all documents and patent documents cited herein is incorporated by reference in their entirety.

EXPERIMENTAL EXAMPLES

An even better understanding of the present invention and of its advantages will be evident from the following experimental examples, offered for illustrative purposes only. The examples are not intended to limit the scope of the present invention in any way.

Materials and Methods

The following materials and methods were used throughout the Examples unless specified otherwise.

General Culture 13 ml with $2.5\times10^5$ cells/ml per vessel in passage 0; $5\times10^5$ cells/ml per vessel at all other passages.

Medium Change: 62% Exchange per day

Cells: TC1133, NINDS

Culture conditions: 37° C., pH 7.4, dO 23.8%, 300 rpm downstirr.

Passaging of the Cells

1. Y27632 treatment of iPSC aggregates at a final concentration of 10 µM two hours before dissociation.
2. Two times washing with Versene: Stop of stirring for two minutes, removal of medium to 2 mL without disturbing sedimented aggregates, addition of Versene to 10 mL, starting the stirring (300 rpm, downwards) for 10 seconds.
3. Removal of medium to 2 mL in the same way as described in the washing steps and addition of Versene to 5 mL.
4. Stirring at 600 rpm for up to 15 min until dissociation is sufficient. In progress controls have to be observed microscopically to assess the right degree of dissociation.
5. Reduce stirring to 300 rpm.
6. Cell count.
7. Transfer a volume of cell suspension into a fresh ambr15 vessel resulting in a seeding concentration of $2\text{-}5\times10^5$ cells/mL, thereby diluting the cell dissociation reagent by addition of an excess volume (at least 5-fold) of iPS-Brew Materials ambr15 cell culture 24 Disposable bioreactors, Low temp, no sparge, Part number: 001-2B81

StemMACS iPS-Brew XF, Basal Medium, Order no.: 130-107-086

StemMACS™ iPS-Brew XF 50× Supplement; Order no.: 130-107-087

ROCKi Y27632; Stemolecule

Versene Solution, Cat No.: 15040-033

Ambr15 bioreactor, Sartorius Stedim

Nucleocounter NC-200 Type 900-0201

Cellavista Cell Imager

Flow Cytometer: BD LSR II Special Order System

Example 1: iPSCs Maintain their Pluripotency in Suspension Culture for at Least 8 Passages and at Least 43 Days The aim of this example was to establish a long-term culture of 8 passages. Hereby, the effects of long-term suspension culture on iPSC quality were assessed. Furthermore, the use of alternative ROCK inhibitor Thiazovivin was tested and compared to Y27632 during passaging of iPSCs in suspension.

Results

Aggregate Size

At the end of all passages except passage 0 aggregates developed a size of about 200 µm (see FIG. 2). The size of ROCKi and TZV treated aggregates were comparable.

Cell Number and Expansion Rates

The expansion rates of iPSCs passaged with TZV were comparable to those of ROCKi treated cells (see FIG. 3). The expansion rate was highest at passage 0 with about 14-fold increase in cell number. In passages 1-5 the expansion rate was about 7-fold and in passages 6-8 it was about 8-fold.

The calculated accumulated expansion rate of ROCKi-treated iPSCs over the complete cultivation time shows an exponential growth (see FIG. 4). An accumulated fold increase of $9.6\times10^6$ after 43 days was reached.

Pluripotency

The expression of pluripotency-related genes (OCT4, TRA-1-60) was high at the end of every analyzed passage in ROCKi treated iPSCs (see FIG. 5). The expression of pluripotency-related genes was also high at the end of passage 0, 2 and 3 in TZV-treated iPSCs (see FIG. 6).

Analysis iPSCs were cultured for 43 days and were automatically passaged 8 times using the cultivation/passaging strategy described herein. No relevant differences have been found between ROCKi- and TZV-treatment during passaging. The iPSCs maintained good quality during the entire run: The aggregate size at the end of passages was around 200 µm.

The expansion rate per passage was about 7-8-fold and the accumulated fold increase after 43 days was about $1\times10^7$. Importantly, the expression of pluripotency-related genes remained high even at passage 8.

SUMMARY

A long-term culture of iPSCs in suspension could surprisingly and successfully be run in for 43 days and 8 passages. A high quality of iPSCs could be shown until passage 8. Most importantly, washing of the iPSCs/removing the cell dissociation reagent after dissociation of the cell aggregates was surprisingly not necessary to maintain a high quality suspension culture for an extended period of time, here 8 passages and 43 days.

Example 2: iPSCs Maintain their Pluripotency in Suspension Culture for at Least 10 Passages and at Least 49 Days Example 2 was performed similar to Example 1 but the suspension culture based on the inventive passaging/cell dissociation method of the invention was extended to 10 passages and 49 days.

Results

Cell Number and Expansion Rates

The calculated accumulated expansion rate over the complete cultivation time shows an exponential growth of iPSCs (see FIG. 7). An accumulated fold increase of $2.9\times10^7$ after 49 days was reached.

Pluripotency

The expression of pluripotency-related genes was high at the end of every analyzed passage (see FIG. 8).

Analysis iPSCs were cultured for 49 days and were automatically passaged 10 times with the cultivation strategy of the invention. The iPSCs maintained good quality during the entire run: The aggregate size at the end of passages that lasted 4-5 days was around the desired 200 μm. The expansion rate was about 8-fold and the accumulated fold increase was $2.9\times10^7$. Importantly, the expression of pluripotency-related genes remained very high (>95%) even at passage 10. Therefore, the results confirm the cultivation strategy.

SUMMARY

For the first time a long-term culture of iPSCs in suspension was run in the ambr15 for 49 days and 10 passages. A high quality of iPSCs was maintained until passage 10.

Example 3: Morphologic Analysis of iPSCs Passaged with the Method of the Invention Example 3 was performed similar to Examples 1 and 2. At day 0, adherent cell culture was transferred into suspension culture. At day 4, the cell aggregates were dissociated. Samples were taken at days 0 (still as adherent culture), 1, 2, 3, and 4 (before and after cell dissociation). FIG. 9 shows light microscope images of these samples comprising the iPSCs. The cells show a normal morphology indicating that the continued cultivation in diluted dissociation reagent does not have any negative impact on the morphology of the cells.

Example 4: Effect of ROCKi Pretreatment

The aim of this example was to analyze the effects of ROCKi pretreatment on passaging of iPSCs in suspension. Example 4 was performed like Examples 1-3 except that the ROCKi pretreatment was performed for 4 h.

Results

Aggregate Size

As shown in FIG. 10, at the day of passaging (day 4 of passage 0) the iPSCs that were to be pretreated with ROCKi were comparable to the iPSCs that were to be passaged without pretreatment regarding aggregate size (197.41±75 μm compared to 200.39±64.05 μm). On day 3 after passaging, aggregates with ROCKi pretreatment were larger than aggregates without ROCKi pretreatment (162.06±53 μm compared to 113.8±49.36 μm).

Expansion Rates

As shown in FIG. 11, at the day of passaging (day 4 of passage 0) the iPSCs that were to be pretreated with ROCKi were comparable to the iPSCs that were to be passaged without pretreatment regarding expansion rate (12.34-fold increase compared to 13.33-fold increase). On day 3 after passaging, iPSCs with ROCKi pretreatment had a higher expansion rate than aggregates without ROCKi pretreatment (3.14-fold increase compared to 1.71-fold increase). The same was found on day 5 after passaging (9.2-fold increase with ROCKi pretreatment compared to 5.08-fold increase without pretreatment).

Pluripotency

As shown in FIG. 12, at the day of passaging (day 4 of passage 0) the iPSCs that were to be pretreated with ROCKi were comparable to the iPSCs that were to be passaged without pretreatment regarding expression of pluripotency-related markers (97.8% OCT4, 96.9% NANOG, 99.3% TRA-1-60 compared to 98.4% OCT4, 97% NANOG, 99.2% TRA-1-60). On day 3 after passaging, iPSCs with ROCKi pretreatment had a higher expression of NANOG than aggregates without ROCKi pretreatment and OCT4 and TRA-1-60 expression was comparable (95.9% OCT4, 93.6% NANOG, 99.1% TRA-1-60 in ROCKi pretreated iPSCs compared to 95.4% OCT4, 61.7% NANOG, 95.2.% TRA-1-60 without pretreatment). On day 5 after passaging, the expression of pluripotency-related markers was comparable between both conditions (94.4% OCT4, 81.8% NANOG, 98.7% TRA-1-60 in ROCKi pretreated iPSCs compared to 95.2% OCT4, 92.4% NANOG, 98.9% TRA-1-60 without pretreatment).

Analysis

The pretreatment with ROCKi before passaging of iPSC aggregates resulted in larger aggregate size and a higher expansion rate in the following passage. Furthermore, the expression of NANOG was higher at an early time point of the following passage in ROCKi pretreated cells, indicating a beneficial effect on the pluripotency status of the iPSCs. Taken together, the results indicate that ROCKi pretreatment before passaging enhances the iPSC expansion and quality during suspension culture.

Example 5: Upscaling of the Method of the Invention

Experimental Design and Experiment Progression:

Passage 0:

- Cells: TC1133 TL004, p4
- Seeding conditions: 450 ml with $2.5\times10^5$ cells/ml.
- Medium change: Start at d2, perfusion 60%.
- Culture conditions: 37° C., pH 7.4, dO 23.8%, 45° blade angle, 120 rpm downstirr (day 0-1) and 100 rpm downstirr (d1-4).

Passage 1-3

Seeding conditions: 320 ml with $2.5\times10^5$ cells/ml.

Medium change: Start at d2, perfusion 60% targeted.

Culture conditions: 37° C., pH 7.4, dO 23.8%, 45° blade angle, 120 rpm downstirr (day 0-1) and 100 rpm downstirr (d1-end of passage).

Passaging Procedure:

The iPSCs were treaded with ROCKi (10 μM final concentration) 2 hours before passaging.

The aggregates were washed two times with 0.5 mM EDTA by letting the aggregates settle to the bottom of the vessel (agitation stop for 2-5 min), aspirating the medium to 50 mL and adding 200 ml EDTA solution.

The aggregates were settled to the bottom of the vessel and the EDTA solution was aspirated to 50 mL as described in the wash steps. 100 mL EDTA solution was added and the aggregates were dissociated by stirring them at 200 rpm for up to 15 min.

When the right dissociation degree was reached (small cell clumps of about 20 cells still remaining), the agitation was reduced to 50 rpm and the cells were counted.

The cell suspension was reduced in the vessel to the volume that is necessary to make the desired cell concentration. The necessary volume of iPS-brew+10 μM ROCKi was added to make the desired cell concentration. Cells were counted and cultivated as described above.

Materials

Reagents and Materials:

StemMACS iPS-Brew XF, Basal Medium, Order no.: 130-107-086

StemMACS iPS-Brew XF 50× Supplement; Order no.: 130-107-087

ROCKi: Y27632 dihydrochloride; Tocris Cat #1254

UltraPure 0.5M EDTA, pH 8.0; Cat #15575020

Devices

Biostat B—DCU II: Type: BB-8841212

Tower 3: Type: BB-8840152 pH Sensor: Hamilton; Easyferm Plus VP 120

Oxygen Sensor: Hamilton; Oxyferm FDA VP 120

UniVessel 0.5 L pH-Meter: Multi 3510 IDS; Xylem Analytics Germany GmbH pH-Elektrode: SenTix Micro 900P; WTVV Nucleocounter NC-200 Type 900-0201

Cellavista

Flow Cytometer: CytoFlex; Beckman Coulter

Results

Here, an 18-day culture was performed in the UniVessel with frequent sampling. The iPSCs were passaged three times. Aggregates with good morphology were observed in all passages (FIG. 13).

The aggregates were large on day 1 of passage 0 with ~120 μm (FIG. 14). On day 4 of passage 0 the aggregates reached a size of ~185 μm. In passage 1 to 3 the aggregates increased from ~100 μm on day 1 to ~200 μm (p1 and 2) or 180 μm (p3) on day 4 or 5, which is in good agreement with the data generated in the ambr15 system.

The expansion rate after 4 days of culture in passage 0 was very good and exceeded the desired 10-fold increase (FIG. 15). The expansion rate in passage 1 and 2 was about 6-fold. In passage 3 the expansion rate was about 9-fold. These findings are in agreement with the long-term culture experiments in the ambr15 system, which also showed lower expansion rates in passages 1 and 2 compared to passage 0 and later passages.

The expression of pluripotency-related genes was high in the inoculum. In suspension culture, the expression of pluripotency-related markers was high in iPSCs at the end of all passages (FIG. 16). Interestingly, a slight increase is seen in OCT4 expression from inoculum to passage 3.

In this example, iPSCs were expanded in a 0.5 L UniVessel for 18 days while maintaining a high culture quality. The iPSCs were successfully passaged three times in the UniVessel without manual processing. The expansion rate was good with about 10-fold increases observed in passages 0 and 4. The aggregate size was about 100 μm at day 1 and reached the desired size of about 200 μm at the end of all passages. Importantly, the expression of pluripotency-related genes was high at the end of all passages. The results show that the expansion strategy that was developed in the ambr15 system was successfully adapted to the UniVessel system.

In this experiment the iPSC expansion strategy was successfully adapted to the UniVessel system, i.e. an upscaling is possible without further modifications. iPSCs of high quality were successfully passaged three times and cultured for 18 days in the UniVessel system having a larger volume than the ambr15 system.

Similar results were also obtained in a 2 L culture system, which further demonstrates that the expansion method of the present invention is very suited for scale-up and large scale production of PSC.

REFERENCES

Burridge, P. W., Holmström, A., and Wu, J. C. (2015). Chemically Defined Culture and Cardiomyocyte Differentiation of Human Pluripotent Stem Cells. Curr. Protoc. Hum. Genet. 87, 21.3.1

Chen, V. C., Ye, J., Shukla, P., Hua, G., Chen, D., Lin, Z., Liu, J., Chai, J., Gold, J., Wu, J., et al. (2015). Development of a scalable suspension culture for cardiac differentiation from human pluripotent stem cells. Stem Cell Res. 15, 365-375.

Kropp et al. "Progress and challenges in large-scale expansion of human pluripotent stem cells" Process Biochemistry, Vol. 59, Part B, August 2017, Pages 244-254.

The invention claimed is:

1. A method of expanding pluripotent stem cells (PSC) in suspension culture in a bioreactor, the method comprising (i) adding an inhibitor of ROCK (ROCKi) to the a suspension culture of aggregated PSC in the bioreactor being cultured in the bioreactor in a medium that has not been supplemented with or comprises a ROCKi, to produce a suspension culture of ROCKi-treated aggregated PSC in the bioreactor;

(ii) adding a cell dissociation agent to the suspension culture of ROCKi-treated aggregated PSC in the bioreactor, thereby dissociating the aggregates of the PSC to produce a suspension culture of disaggregated ROCKi-treated PSC in the bioreactor, wherein the dissociation agent is a chelating agent;

(iii) diluting the cell dissociation agent added in step (ii) by adding an excess volume of culture medium to the suspension culture of disaggregated ROCKi-treated PSC in the bioreactor sufficient to decrease the concentration of the cell dissociation agent to a concentration at which aggregates of PSC can form again, wherein the excess volume of culture medium added comprises the ROCKi;

(iv) culturing of the mixture obtained in step (iii) under suitable conditions that allow the expansion of the PSCs and formation of aggregated PSC; and (v) exchanging the medium to a cell culture medium that has not been supplemented or comprises a ROCKi.

2. The method of claim 1, wherein the chelating agent is selected from the group consisting of ethylenediaminetetraacetate (EDTA), ethylene glycol-bis (β-aminoethyl ether)-N,N,N',N'-tetraacetic acid (EGTA), iminodisuccinic acid (IDS), polyaspartic acid, ethylenediamine-N,N'-disuccinic acid (EDDS), citrate, citric acid, 1,2-bis (o-aminophenoxy) ethane-N,N,N',N'-tetraacetic acid (BAPTA), methylglycinediacetic acid (MGDA) and combinations thereof.

3. The method of claim 2, wherein the cell dissociation reagent is EDTA.

4. The method of claim 3, wherein the final concentration of EDTA in step (ii) is at least 100 μM EDTA, in a range of about 100 to about 1000 μM EDTA, in a range of about 250 to about 750 μM EDTA, in a range of about 400 to about 600 μM EDTA or is about 500 μM EDTA.

5. The method of claim 3, wherein the concentration of EDTA in step (iii) after adding the excess volume of culture medium is about 100 μM or less, about 95 μM or less, about 90 μM or less, about 80 μM or less, about 70 μM or less, in a range of about 100 to about 1 μM EDTA, or in a range of about 90 to about 1 μM EDTA.

6. The method of claim 1, wherein the excess volume exceeds the volume of the cell dissociation agent by at least 5 times.

7. The method of claim 1, wherein step (iv) is performed for about 1 to about 3 days.

8. The method of claim 1, wherein step (v) starts about 1 to about 3 days after step (iii).

9. The method of claim 1, wherein the ROCKi is selected from the group consisting of AS1892802, fasudil hydrochloride, GSK 269962, GSK 429286, H 1152, HA 1100, OXA 06, RKI 1447, SB 772077B, SR 3677, TC-S 7001, thiazovivin Y27632 and combinations thereof.

10. The method of claim 1, wherein the ROCKi is Y27632.

11. The method of claim 10, wherein Y27632 is added to a final concentration of about 10 μM.

12. 1 The method of claim 1, wherein the ROCKi is added in step about 4 hours or less prior to step (ii).

13. The method of claim 1, wherein the addition of an excess volume of the culture medium in step (iii) results in a cell number of about $1\times10^5$ to about $1\times10^6$ cells/ml, about 1.5 to about $7.5\times10^5$ cells/ml, about $2\times10^5$ to about $5\times10^5$ cells/ml, about $2\times10^5$ to about $3\times10^5$ cells/ml or about $2.5\times10^5$ cells/ml in the culture medium.

14. The method of claim 1, wherein the culture medium in steps (i) and (iii) is identical.

15. The method of claim 1, wherein the temperature of the culture medium is about 30 to 50° C., about 35 to 40° C., about 36to 38° C. or about 37° C.

16. The method of claim 1, wherein steps (i) to (v) are repeated once, twice, 3 times, 4 times, 5 times, at least 5 times, or at least 10 times.

17. The method of claim 1, wherein the pluripotent stem cells are selected from the group consisting of induced pluripotent stem cells (iPSC), embryonic stem cells (ESC), parthenogenetic stem cells (pPSC) and nuclear transfer derived PSCs (ntPSC).

18. The method of claim 16, wherein the PSCs maintain their pluripotency after each repetition of steps (i) to (v).

19. The method of claim 1, wherein the pluripotent stem cells are TC-1133 cells.

20. The method of claim 1, wherein the aggregates in step (ii) have an average diameter of about 180 μm to about 250 μm.

21. The method of claim 1, wherein the aggregates are dissociated in step (ii) for at least about 1 min, at least about 2 min, at least about 3 min, at least about 5 min, at least about 10 min, for 1 to 20 min, for about 10 to about 20 min, for about 10 to about 15 min or for up to about 15 min.

22. The method of claim 1, wherein steps (i)-(v) are performed in a closed system.

23. The method of claim 1, wherein step (iv) is performed for about 2 days, step (v) is performed for about 2 days, and the ROCKi is added in step (i) about 4 hours or less prior to step (ii).

* * * * *